United States Patent
Kassab et al.

(10) Patent No.: US 10,568,546 B2
(45) Date of Patent: Feb. 25, 2020

(54) DEVICES AND METHODS FOR SIZING VALVE APERTURES AND LUMINAL ORGANS

(71) Applicants: 3DT Holdings, LLC, San Diego, CA (US); H. Toby Markowitz, Roseville, MN (US)

(72) Inventors: Ghassan S. Kassab, La Jolla, CA (US); H. Toby Markowitz, Roseville, MN (US)

(*) Notice: Subject to any disclaimer, the term of this patent is extended or adjusted under 35 U.S.C. 154(b) by 49 days.

(21) Appl. No.: 14/742,025

(22) Filed: Jun. 17, 2015

(65) Prior Publication Data

US 2015/0366485 A1    Dec. 24, 2015

Related U.S. Application Data

(60) Continuation-in-part of application No. 14/688,624, filed on Apr. 16, 2015, and a continuation-in-part of
(Continued)

(51) Int. Cl.
*A61B 5/107* (2006.01)
*A61B 5/00* (2006.01)
(Continued)

(52) U.S. Cl.
CPC .......... *A61B 5/1076* (2013.01); *A61B 5/0538* (2013.01); *A61B 5/6853* (2013.01);
(Continued)

(58) Field of Classification Search
CPC . A61B 5/1076; A61B 5/02007; A61B 5/6852; A61B 5/6859; A61B 5/6885; A61B 5/6886
See application file for complete search history.

(56) References Cited

U.S. PATENT DOCUMENTS 3,896,373 A    7/1975  Zelby
4,380,237 A    4/1983  Newbower
(Continued)

FOREIGN PATENT DOCUMENTS

EP    1 025 805 A1    8/2000
WO    WO 98/35611 A1    8/1998
(Continued)

OTHER PUBLICATIONS

International Searching Authority, International Search Report, dated Jul. 6, 2005 (PCT/US04/04828).
(Continued)

*Primary Examiner* — Devin B Henson
(74) *Attorney, Agent, or Firm* — Reichel Stohry Dean LLP; Mark C. Reichel; Natalie J. Dean

(57) ABSTRACT

Devices and methods for sizing valve apertures and luminal organs. In at least one embodiment of a device for obtaining measurements within a luminal organ of the present disclosure, the device comprises an elongated body, and at least one sizing finger positioned at a distal end of the elongated body, the at least one sizing finger configured to move from a first position to a second position by way of adjustment of at least one movable device coupled thereto, wherein a dimensional measurement within the luminal organ can be determined based upon the first position and the second position.

13 Claims, 22 Drawing Sheets

Related U.S. Application Data application No. 13/850,758, filed on Mar. 26, 2013, which is a continuation of application No. 12/706,677, filed on Feb. 16, 2010, now Pat. No. 8,406,867, which is a continuation-in-part of application No. 11/891,981, filed on Aug. 14, 2007, now Pat. No. 8,114,143, which is a division of application No. 10/782,149, filed on Feb. 19, 2004, now Pat. No. 7,454,244.

(60) Provisional application No. 60/502,139, filed on Sep. 11, 2003, provisional application No. 60/493,145, filed on Aug. 7, 2003, provisional application No. 60/449,266, filed on Feb. 21, 2003, provisional application No. 61/980,364, filed on Apr. 16, 2014, provisional application No. 62/013,239, filed on Jun. 17, 2014.

(51) Int. Cl.
*A61B 5/053* (2006.01)
*A61B 5/02* (2006.01)

(52) U.S. Cl.
CPC ........ *A61B 5/6886* (2013.01); *A61B 5/02007* (2013.01); *A61B 5/6852* (2013.01); *A61B 5/6859* (2013.01); *A61B 5/6885* (2013.01)

(56) References Cited

U.S. PATENT DOCUMENTS

| | | | |
|---|---|---|---|
| 4,587,975 A | 5/1986 | Salo et al. | |
| 4,840,182 A | 6/1989 | Carlson | |
| 4,873,987 A | 10/1989 | Djordjevich et al. | |
| 4,957,110 A | 9/1990 | Vogel et al. | |
| 5,058,583 A | 10/1991 | Geddes et al. | |
| 5,125,410 A | 6/1992 | Misono et al. | |
| 5,233,994 A | 8/1993 | Shmulewitz | |
| 5,366,443 A | 11/1994 | Eggers et al. | |
| 5,453,576 A | 9/1995 | Krivitski | |
| 5,665,103 A | 9/1997 | Lafontaine et al. | |
| 5,827,192 A | 10/1998 | Gopakumaran et al. | |
| 5,842,998 A | 12/1998 | Gopakumaran et al. | |
| 5,971,933 A | 10/1999 | Schlueter et al. | |
| 6,112,115 A | 8/2000 | Feldman et al. | |
| 6,165,977 A | 12/2000 | Mochly-Rosen | |
| 6,187,744 B1 | 2/2001 | Rooney | |
| 6,191,136 B1 | 2/2001 | Marban | |
| 6,270,493 B1 | 8/2001 | Lalonde et al. | |
| 6,296,615 B1 | 10/2001 | Brockway et al. | |
| 6,325,762 B1 | 12/2001 | Tjin | |
| 6,354,999 B1 | 3/2002 | Dgany et al. | |
| 6,360,123 B1 | 3/2002 | Kimchi et al. | |
| 6,398,738 B1 | 6/2002 | Millar | |
| 6,406,422 B1 | 6/2002 | Landesberg | |
| 6,427,351 B1* | 8/2002 | Matthews | A61B 5/1076 33/512 |
| 6,471,656 B1 | 10/2002 | Shalman et al. | |
| 6,494,832 B1 | 12/2002 | Feldman et al. | |
| 6,511,413 B2 | 1/2003 | Landesberg | |
| 6,545,678 B1 | 4/2003 | Ohazama | |
| 6,569,862 B1 | 5/2003 | Marban | |
| 6,663,661 B2 | 12/2003 | Boneau | |
| 6,666,828 B2 | 12/2003 | Greco et al. | |
| 6,926,674 B2 | 8/2005 | Tenerz et al. | |
| 7,069,072 B2 | 6/2006 | Jensen et al. | |
| 7,077,812 B2* | 7/2006 | Naghavi | A61B 5/01 600/587 |
| 7,141,019 B2 | 11/2006 | Pearlman | |
| 7,155,270 B2* | 12/2006 | Solis | A61B 18/1492 600/374 |
| 7,169,107 B2 | 1/2007 | Jersey-Willuhn et al. | |
| 7,189,208 B1 | 3/2007 | Beatty et al. | |
| 7,236,820 B2 | 6/2007 | Mabary et al. | |
| 7,311,702 B2 | 12/2007 | Tallarida et al. | |
| 7,326,241 B2 | 2/2008 | Jang | |
| 7,479,120 B2 | 1/2009 | Gregersen | |
| 7,615,014 B2* | 11/2009 | Omata | A61B 5/103 600/587 |
| 8,078,274 B2 | 12/2011 | Kassab | |
| 8,114,143 B2 | 2/2012 | Djordjevich et al. | |
| 8,277,395 B2* | 10/2012 | Griego | A61B 5/1076 600/587 |
| 8,588,886 B2* | 11/2013 | de la Rama | A61B 18/1492 600/374 |
| 9,579,149 B2* | 2/2017 | Kelly | A61B 18/1492 |
| 2002/0049488 A1 | 4/2002 | Boneau | |
| 2002/0062149 A1 | 5/2002 | Jang | |
| 2003/0013986 A1 | 1/2003 | Saadat | |
| 2004/0024329 A1 | 2/2004 | Jansen et al. | |
| 2004/0044286 A1 | 3/2004 | Hossack et al. | |
| 2004/0116816 A1 | 6/2004 | Tenerz et al. | |
| 2004/0230131 A1 | 11/2004 | Kassab et al. | |
| 2004/0254495 A1 | 12/2004 | Mabary et al. | |
| 2007/0161914 A1 | 7/2007 | Zdeblick et al. | |
| 2008/0033316 A1 | 2/2008 | Kassab et al. | |
| 2008/0176271 A1 | 7/2008 | Silver et al. | |
| 2008/0194996 A1 | 8/2008 | Kassab | |
| 2008/0269581 A1 | 10/2008 | Wood et al. | |
| 2009/0216133 A1 | 8/2009 | Kassab | |
| 2010/0041984 A1 | 2/2010 | Shapeland et al. | |
| 2013/0018281 A1* | 1/2013 | Nagale | A61B 5/205 600/587 |
| 2015/0223757 A1* | 8/2015 | Werneth | A61B 5/6852 600/301 |

FOREIGN PATENT DOCUMENTS

| | | |
|---|---|---|
| WO | WO 02/19905 | 3/2002 |
| WO | WO 02/085442 A1 | 10/2002 |
| WO | WO 03/092495 A1 | 11/2003 |

OTHER PUBLICATIONS

International Searching Authority, Written Opinion, dated Jul. 6, 2005 (PCT/US04/04828).

International Searching Authority, International Search Report, dated Aug. 8, 2007 (PCT/US06/05985).

International Searching Authority, Written Opinion, dated Aug. 8, 2007 (PCT/US06/05985).

European Patent Office, Supplementary European Search Report, dated Aug. 3, 2007 (EP 04 71 2383).

International Searching Authority, International Search Report, dated Jun. 28, 2010, (PCT/US10/031553).

International Searching Authority, International Search Report, dated Apr. 4, 2011 (PCT/US11/023911).

International Searching Authority, Written Opinion, dated Apr. 4, 2011 (PCT/US11/023911).

International Searching Authority, International Search Report, dated Jul. 7, 2011 (PCT/US11/024961).

International Searching Authority, Written Opinion, dated Jul. 7, 2011 (PCT/US11/024961).

International Searching Authority, International Search Report, dated Apr. 19, 2011 (PCT/US11/026337).

International Searching Authority, Written Opinion, dated Apr. 19, 2011(PCT/US11/026337).

International Searching Authority, Preliminary Report on Patentability, dated Nov. 3, 2011 (PCT/US2010/032178).

Hoekstein and Inbar, "Cardiac Stroke Volume Estimation . . . Impedance Measurements." Technion Department of Electrical Engineering Publication EE Pub No. 911, Feb. 1994.

L. Kornet, et al. "Conductance Method for the Measurement of Cross-Sectional Areas of the Aorta," Annals of Biomedical Engineering, vol. 27, pp. 141-150, 1999.

Douglas A. Hettrick, et al., "Finite Element Model . . . Diameter Via Conductance," Annals of Biomedical Engineering, vol. 27, pp. 151-159, 1999.

(56) References Cited

OTHER PUBLICATIONS

Douglas A. Hettrick, et al., "In Vivo Measurement of Real-Time . . . Conductance Catheter," Annals of Biomedical Engineering, vol. 26, pp. 431-440, 1998.
International Searching Authority, Written Opinion, dated Jun. 28, 2010, (PCT/US10/031553).

* cited by examiner

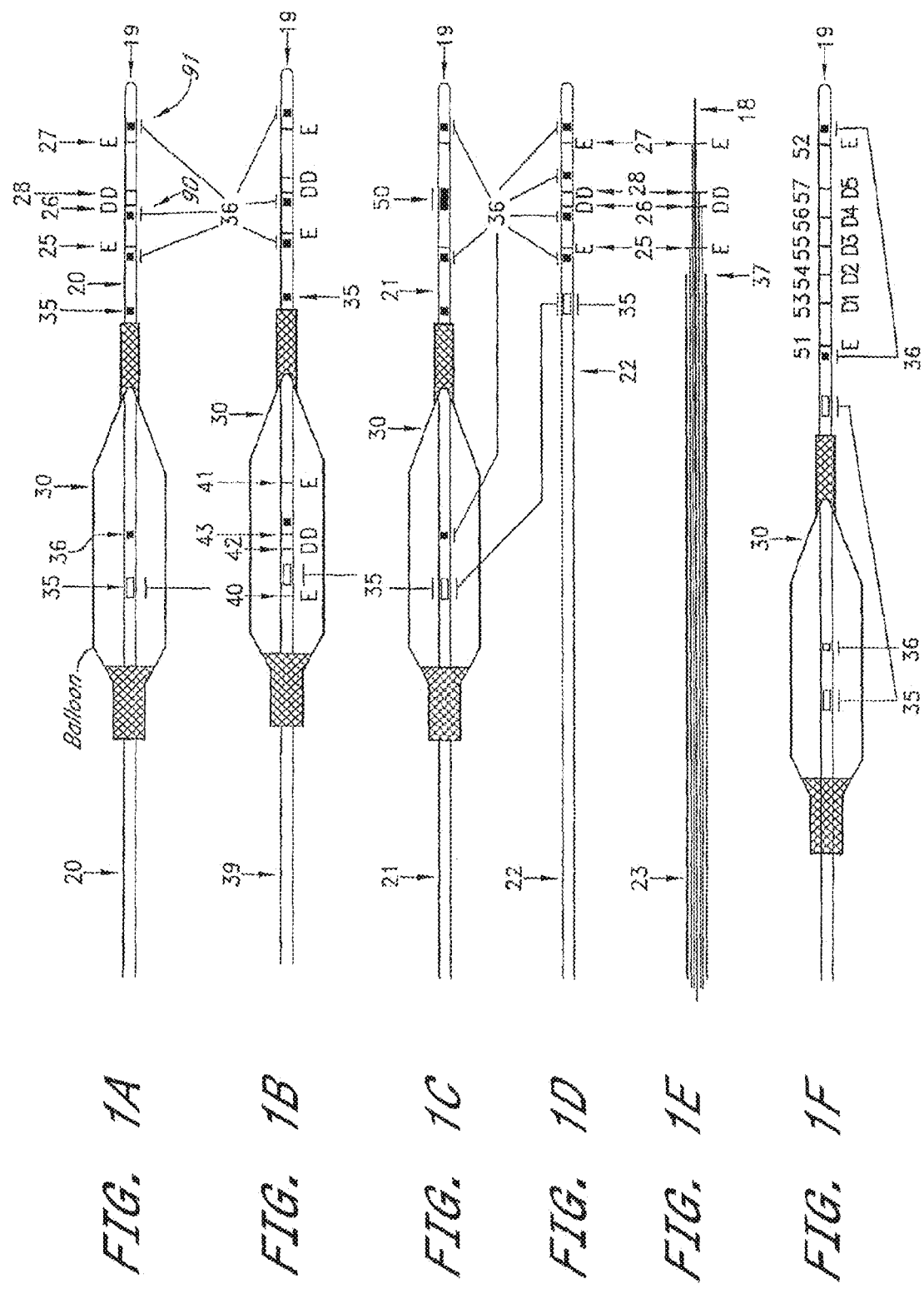

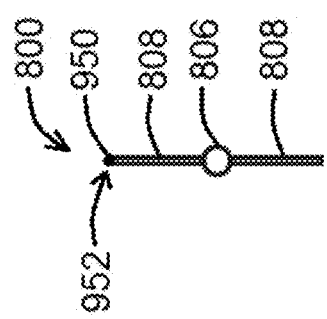
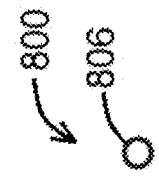
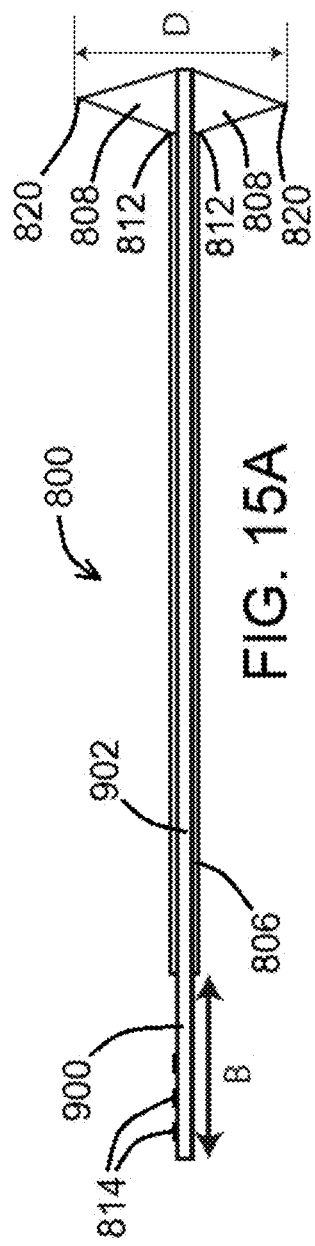
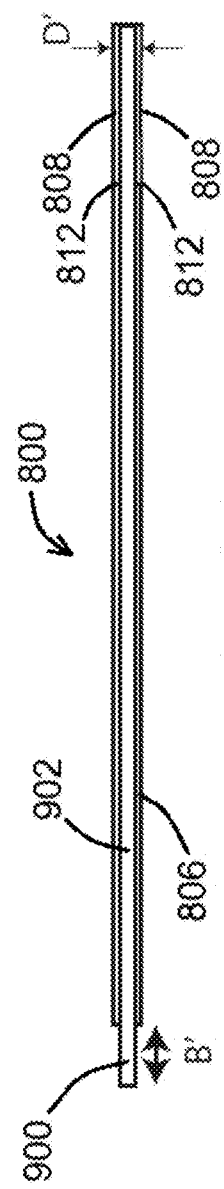

DEVICES AND METHODS FOR SIZING VALVE APERTURES AND LUMINAL ORGANS

PRIORITY

The present application a) is related to, and claims the priority benefit of, U.S. Provisional Patent Application Ser. No. 62/013,239, filed Jun. 16, 2014; b) is related to, and claims the priority benefit of, and is a U.S. continuation-in-part application of, U.S. patent application Ser. No. 13/850,758, filed on Mar. 26, 2013, which is related to, claims the priority benefit of, and is a continuation application of, U.S. patent application Ser. No. 12/706,677, filed Feb. 16, 2010 and issued as U.S. Pat. No. 8,406,867 on Mar. 26, 2013, which is related to, claims the priority benefit of, and is a continuation-in-part application of, U.S. patent application Ser. No. 11/891,981, filed Aug. 14, 2007 and issued as U.S. Pat. No. 8,114,143 on Feb. 14, 2012, which is related to, claims the priority benefit of, and is a divisional application of, U.S. patent application Ser. No. 10/782,149, filed Feb. 19, 2004 and issued as U.S. Pat. No. 7,454,244 on Nov. 18, 2008, which is related to, and claims the priority benefit of, U.S. Provisional Patent Application Ser. No. 60/449,266, filed Feb. 21, 2003, U.S. Provisional Patent Application Ser. No. 60/493,145, filed Aug. 7, 2003, and U.S. Provisional Patent Application Ser. No. 60/502,139, filed Sep. 11, 2003; and c) is related to, claims the priority benefit of, and is a U.S. continuation-in-part application of, U.S. patent application Ser. No. 14/688,624, filed on Apr. 16, 2015, which is related to, and claims the priority benefit of, U.S. Provisional Patent Application Ser. No. 61/980,364, filed Apr. 16, 2014. The contents of each of these applications and patents are hereby incorporated by reference in their entirety into this disclosure.

BACKGROUND

Coronary heart disease (CHD) is commonly caused by atherosclerotic narrowing of the coronary arteries and is likely to produce angina pectoris, heart attacks or a combination. CHD caused 466,101 deaths in the USA in 1997 and is one of the leading causes of death in America today. Approximately, 12 million people alive today have a history of heart attack, angina pectoris or both. The break down for males and females is 49% and 51%, respectively. This year, an estimated 1.1 million Americans will have a new or recurrent coronary attack, and more than 40% of the people experiencing these attacks will die as a result. About 225,000 people a year die of coronary attack without being hospitalized. These are sudden deaths caused by cardiac arrest, usually resulting from ventricular fibrillation. More than 400,000 Americans and 800,000 patients world-wide undergo a non-surgical coronary artery interventional procedure each year. Although only introduced in the 1990s, in some laboratories intra-coronary stents are used in 90% of these patients.

Stents increase minimal coronary lumen diameter to a greater degree than percutaneous transluminal coronary angioplasty (PTCA) alone according to the results of two randomized trials using the Palmaz-Schatz stent. These trials compared two initial treatment strategies: stenting alone and PTCA with "stent backup" if needed. In the STRESS trial, there was a significant difference in successful angiographic outcome in favor of stenting (96.1% vs. 89.6%).

Intravascular Ultrasound

Currently intravascular ultrasound is the method of choice to determine the true diameter of the diseased vessel in order to size the stent correctly. The term "vessel," as used herein, refers generally to any hollow, tubular, or luminal organ. The tomographic orientation of ultrasound enables visualization of the full 360° circumference of the vessel wall and permits direct measurements of lumen dimensions, including minimal and maximal diameter and cross-sectional area. Information from ultrasound is combined with that obtained by angiography. Because of the latticed characteristics of stents, radiographic contrast material can surround the stent, producing an angiographic appearance of a large lumen, even when the stent struts are not in full contact with the vessel wall. A large observational ultrasound study after angiographically guided stent deployment revealed an average residual plaque area of 51% in a comparison of minimal stent diameter with reference segment diameter, and incomplete wall apposition was frequently observed. In this cohort, additional balloon inflations resulted in a final average residual plaque area of 34%, even though the final angiographic percent stenosis was negative (20.7%). These investigators used ultrasound to guide deployment.

However, using intravascular ultrasound as mentioned above requires a first step of advancement of an ultrasound catheter and then withdrawal of the ultrasound catheter before coronary angioplasty thereby adding additional time to the stent procedure. Furthermore, it requires an ultrasound machine. This adds significant cost and time and more risk to the procedure.

Aortic Stenosis

Aortic Stenosis (AS) is one of the major reasons for valve replacements in adult. AS occurs when the aortic valve orifice narrows secondary to valve degeneration. The aortic valve area is reduced to one fourth of its normal size before it shows a hemodynamic effect. Because the area of the normal adult valve orifice is typically 3.0 to 4.0 $cm^2$, an area 0.75-1.0 $cm^2$ is usually not considered severe AS. When stenosis is severe and cardiac output is normal, the mean trans-valvular pressure gradient is generally >50 mmHg. Some patients with severe AS remain asymptomatic, whereas others with only moderate stenosis develop symptoms. Therapeutic decisions, particularly those related to corrective surgery, are based largely on the presence or absence of symptoms.

The natural history of AS in the adult consists of a prolonged latent period in which morbidity and mortality are very low. The rate of progression of the stenotic lesion has been estimated in a variety of hemodynamic studies performed largely in patients with moderate AS. Cardiac catheterization and Doppler echocardiographic studies indicate that some patients exhibit a decrease in valve area of 0.1-0.3 $cm^2$ per year; the average rate of change is 0.12 $cm^2$ per year. The systolic pressure gradient across the valve may increase by as much as 10 to 15 mmHg per year. However, more than half of the reported patients showed little or no progression over a 3-9 year period. Although it appears that progression of AS can be more rapid in patients with degenerative calcific disease than in those with congenital or rheumatic disease, it is not possible to predict the rate of progression in an individual patient.

Eventually, symptoms of angina, syncope, or heart failure develop after a long latent period, and the outlook changes dramatically. After onset of symptoms, average survival is <2-3 years. Thus, the development of symptoms identifies a critical point in the natural history of AS.

Many asymptomatic patients with severe AS develop symptoms within a few years and require surgery. The incidence of angina, dyspnea, or syncope in asymptomatic patients with Doppler outflow velocities of 4 m/s has been reported to be as high as 38% after 2 years and 79% after 3 years. Therefore, patients with severe AS require careful monitoring for development of symptoms and progressive disease.

Indications for Cardiac Catheterization

In patients with AS, the indications for cardiac catheterization and angiography are to assess the coronary circulation (to confirm the absence of coronary artery disease) and to confirm or clarify the clinical diagnosis of AS severity. If echocardiographic data are typical of severe isolated. AS, coronary angiography may be all that is needed before aortic valve replacement (AVR). Complete left- and right-heart catheterization may be necessary to assess the hemodynamic severity of AS if there is a discrepancy between clinical and echocardiographic data or evidence of associated valvular or congenital disease or pulmonary hypertension.

The pressure gradient across a stenotic valve is related to the valve orifice area and transvalvular flow through Bernoulli's principle. Thus, in the presence of depressed cardiac output, relatively low pressure gradients are frequently obtained in patients with severe AS. On the other hand, during exercise or other high-flow states, systolic gradients can be measured in minimally stenotic valves. For these reasons, complete assessment of AS requires (1) measurement of transvalvular flow, (2) determination of the transvalvular pressure gradient, and (3) calculation of the effective valve area. Careful attention to detail with accurate measurements of pressure and flow is important, especially in patients with low cardiac output or a low transvalvular pressure gradient.

Problems with Current Aortic Valve Area Measurements

Patients with severe AS and low cardiac output are often present with only modest transvalvular pressure gradients (i.e., <30 mmHg). Such patients can be difficult to distinguish from those with low cardiac output and only mild to moderate AS. In both situations, the low-flow state and low pressure gradient contribute to a calculated effective valve area that can meet criteria for severe AS. The standard valve area formula (simplified Hakki formula which is valve area=cardiac output/[pressure gradient]$^{1/2}$) is less accurate and is known to underestimate the valve area in low-flow states; under such conditions, it should be interpreted with caution. Although valve resistance is less sensitive to flow than valve area, resistance calculations have not been proved to be substantially better than valve area calculations.

In patients with low gradient stenosis and what appears to be moderate to severe AS, it may be useful to determine the transvalvular pressure gradient and calculate valve area and resistance during a baseline state and again during exercise or pharmacological (i.e., dobutamine infusion) stress. Patients who do not have true, anatomically severe stenosis exhibit an increase in the valve area during an increase in cardiac output. In patients with severe AS, these changes may result in a calculated valve area that is higher than the baseline calculation but that remains in the severe range, whereas in patients without severe AS, the calculated valve area will fall outside the severe range with administration of dobutamine and indicate that severe AS is not present.

There are many other limitations in estimating aortic valve area in patients with aortic stenosis using echocardiography and cardiac catheterization. Accurate measurement of the aortic valve area in patients with aortic stenosis can be difficult in the setting of low cardiac output or concomitant aortic or mitral regurgitations. Concomitant aortic regurgitation or low cardiac output can overestimate the severity of aortic stenosis. Furthermore, because of the dependence of aortic valve area calculation on cardiac output, any under or overestimation of cardiac output will cause inaccurate measurement of valve area. This is particularly important in patients with tricuspid regurgitation. Falsely measured aortic valve area could cause inappropriate aortic valve surgery in patients who do not need it.

Other Visceral Organs

Visceral organs such as the gastrointestinal tract and the urinary tract serve to transport luminal contents (fluids) from one end of the organ to the other end or to an absorption site. The esophagus, for example, transports swallowed material from the pharynx to the stomach. Diseases may affect the transport function of the organs by changing the luminal cross-sectional area, the peristalsis generated by muscle, or by changing the tissue components. For example, strictures in the esophagus and urethra constitute a narrowing of the organ where fibrosis of the wall may occur. Strictures and narrowing can be treated with distension, much like the treatment of plaques in the coronary arteries.

Valve Sizing and Replacement

In addition, percutaneous interventional therapy has been an option for patients with pulmonic, mitral, and aortic valvular disease for decades. The treatment preferred in selected patients with pulmonic or mitral stenosis is percutaneous valvuloplasty. According to the current ACC/American Heart Association (AHA) guidelines, in patients with calcific aortic stenosis, balloon aortic valvuloplasty (BAV) has been used as a bridge to aortic valve replacement.

Hospital mortality for BAV varies from 3.5% to 13.5%, while serious complications appear in at least 25% of the patients. The durability of BAV is restricted. Consequently, open aortic valve replacement continues to be the best therapy for aortic stenosis (AS) in patients who are viable candidates for surgery. The most frequent heart valve operation is the aortic valve replacement. In the United States, from 2% to 7% of individuals older than 65 years suffer from AS, which will continue to increase as more people live longer. AS is frequently associated with comorbid risk factors and previous bypass surgery since it is persistently progressive and it takes place in elderly patients. The surgical therapy for AS patients is useful to improve symptoms and prolong life.

Percutaneous strategies for the treatment of AS began with percutaneous balloon valvuloplasty. Data from the multicenter National Heart, Lung, and Blood Institute (NHLBI) registry, however, showed only a mild progress in early hemodynamics, a significant incidence of peripheral vascular complications, a 30 day mortality of 7%, and a high incidence of restenosis within 6 months.

The unsatisfactory BAV results have led to the investigation of percutaneous placement of prosthetic aortic valves. Devices to perform the same have been clinically utilized in a small number of cases in high-risk patients. Although percutaneous aortic valve insertion has been performed on extremely high-risk patients, considerable para-valvular leak regurgitation and early mortality discourage the approach.

One concern with percutaneous or transapical aortic valve replacement is the sizing of dilatation of the calcific aortic valve prior to delivery of the stent valve device. The consequences of incorrect sizing of the aortic valve area are periprosthetic leak, calcium embolization, and difficulties in the insertion of the device and its possible migration.

Ischemic mitral regurgitation (IMR) is a mitral valve insufficiency that is produced by acute myocardial infarction (AMI) and later infarction-induced left ventricular remodeling. Approximately 1.2 to 2.1 million patients in the United States suffer IMR, including more than 400,000 patients running moderate-to-severe MR. It is estimated that about 50-60% of congestive heart failure (CHF) patients suffer from some type of mitral regurgitation (MR). The valve is structurally normal in the vast majority of these patients.

In end-stage heart failure patient, the mechanism of MR is multifactorial and it is related to changes in left ventricular (LV) geometry, with a subsequent displacement of the subvalvular apparatus, annular dilatation, and restrictive leaflet motion, which ends in failure of the leaflet coaptation. Physiologically, IMR in these patients will lead to LV overload and decrease of stroke volume.

Numerous investigators support the use of a stringent restrictive ring (which is two sizes smaller than the measured size) in order to obtain better leaflet coaptation. This avoids MR recurrence and promotes reverse remodeling. Midterm follow-up (18 months) with this approach shows reverse remodeling in 58% of patients. During direct visualization in surgery, the sizing of the annulus can be accurately determined and made appropriate for each patient.

Patients with MR have a considerably diminished survival at 2 years' follow-up versus patients lacking mitral regurgitation. Furthermore, the severity of mitral regurgitation is directly associated to mortality risk. The undersizing of the mitral annulus will lead to acute valuable geometric changes of the base of the left ventricle, which might diminish LV volume and wall stress. When mitral regurgitation is treated conservatively morbidity and mortality is high.

It seems logical to correct mitral regurgitation in patients with end-stage heart failure (HF) in order to improve prognosis. However, and at the present time, mitral annuloplasty is not routinely performed in these patients due to significant mortality and elevated recurrence rates. On the other hand, numerous recent investigations have demonstrated somewhat low operative mortality suggesting improved long-term survival after stringent restrictive mitral annuloplasty.

Surgical approaches to MR include mitral valve replacement and repair, with the latest studies supporting early repair in structural MR when possible or in patients with ischemic MR and symptomatic HF but morbidity, mortality, and late recurrent mitral regurgitation limit extensive surgical repair application. Surgical mitral repair could be sophisticated and complex, but the majority of repairs currently consist of simple annuloplasty.

Recently, percutaneous approaches to mitral annuloplasty as well as percutaneous replacement of mitral valve have been shown to reduce MR of global left ventricular dysfunction, acute ischemia, and chronic post-infarction. A number of devices have been described to remodel or replace the mitral annulus to decrease annular anteroposterior diameter.

The possibility of balloon sizing of valve annulus prior to committing to a particular size valve is essential. Furthermore, the sizing of the stent valve during delivery will ensure good apposition and prevent leak, migration or erosion over the long term.

Thus, a need exists in the art for an alternative to the conventional devices and methods for sizing a valve annulus for the subsequent replacement of mitral valves, for example. A further need exists for a reliable, accurate and minimally invasive system or technique of sizing a percutaneous valve and/or a valve annulus and positioning a stent valve therein.

BRIEF SUMMARY

In at least one embodiment of a method to size a valve annulus of the present disclosure, the method comprises the steps of introducing at least part of a sizing device into a luminal organ at a valve annulus, the sizing device having a detector and a pressure transducer within a balloon positioned at or near a distal end of the detection device, inflating the balloon until a threshold pressure is detected by the pressure transducer within the balloon, obtaining a first valve annulus measurement using the detector, and withdrawing the sizing device from the luminal organ. In another embodiment, the method further comprises the steps of positioning a stent valve upon the balloon, reintroducing at least part of a sizing device into the luminal organ at the valve annulus, and reinflating the balloon to the first valve annulus measurement to place the stent valve within the valve annulus. In yet another embodiment, the method further comprises the step of rewithdrawing the sizing device from the luminal organ.

In at least one embodiment of a method to size a valve annulus of the present disclosure, the sizing device further comprises a catheter having a lumen therethrough and defining a suction/infusion port within the catheter within the balloon. In an additional embodiment, the step of inflating the balloon comprises introducing a fluid into the lumen of the catheter, through the suction/infusion port, and into the balloon. In another embodiment, the step of withdrawing the sizing device comprises removing fluid from the balloon, through the suction/infusion port, and into the lumen of the catheter, to deflate the balloon. In yet another embodiment, the detector comprises two detection electrodes positioned in between two excitation electrodes, the excitation electrodes capable of producing an electric field to facilitate a conductance measurement of a fluid within the balloon. In an additional embodiment, the step obtaining a first valve annulus measurement comprises obtaining a balloon cross sectional area using the detector.

In at least one embodiment of a method to size a valve annulus of the present disclosure, the step of obtaining a first valve annulus measurement comprises measuring a balloon cross-sectional area using the detector when the threshold pressure is present within the balloon. In another embodiment, the balloon cross-sectional area is determined from a conductance measurement of a fluid present within the balloon obtained by the detector, a known conductivity of the fluid, and a known distance between two detection electrodes of the detector.

In at least one embodiment of a method to size a valve annulus of the present disclosure, the step of inflating the balloon comprises injecting a solution having a known conductivity into the balloon. In another embodiment, the step of obtaining a first valve annulus measurement comprises measuring a cross-sectional area based in part of the conductivity of the fluid and a conductance value obtained using the detector.

In at least one embodiment of a device to size a valve annulus of the present disclosure, the device comprises an elongated body extending from a proximal end to a distal end and having a lumen therethrough, a balloon positioned along the elongated body at or near the distal end, a detector and a pressure transducer positioned along the elongated body within the balloon, and a suction/infusion port defined within the elongated body within the balloon.

In at least one embodiment, the detector comprises a pair of excitation electrodes located on the elongated body, and a pair of detection electrodes located on the elongated body in between the pair of excitation electrodes, wherein the detector is capable of obtaining a conductance measurement of a fluid within the balloon. In another embodiment, the pair of excitation electrodes are capable of producing an electrical field, and wherein the pair of detection electrodes are capable of measuring an conductance of the fluid within the balloon. In an additional embodiment, at least one excitation electrode of the pair of excitation electrodes is/are in communication with a current source capable of supplying electrical current to the at least one excitation electrode.

In at least one embodiment of a device to size a valve annulus of the present disclosure, the device further comprises a data acquisition and processing system capable of receiving conductance data from the pair of detection electrodes. In an additional embodiment, the data acquisition and processing system is further capable of calculating a first valve annulus measurement within the balloon based from the conductance measurement of the fluid within the balloon obtained by the detector, a known conductivity of the fluid, and a known distance between the pair of detection electrodes. In another embodiment, the pressure transducer is capable of detecting a pressure within the balloon. In yet another embodiment, the suction/infusion port is in communication with the lumen of the elongated body, thereby enabling injection of a solution into the lumen of the elongated body, through the suction/infusion port, and into the balloon. In various embodiments, the lumen of the elongated body is in communication with a source of a solution to be injected therethrough and through the suction/infusion port into the balloon. In an additional embodiment, when a fluid is injected through the lumen of the elongated body into the balloon, the detector is capable of obtaining a fluid conductance measurement within the balloon, wherein the fluid conductance measurement is useful to determine balloon cross-sectional area.

In at least one embodiment of a system to size a valve annulus of the present disclosure, the system comprises a device comprising an elongated body extending from a proximal end to a distal end and having a lumen therethrough, a balloon positioned along the elongated body at or near the distal end, a detector and a pressure transducer positioned along the elongated body within the balloon, and a suction/infusion port defined within the elongated body within the balloon, the system also comprising a current source coupled to the detector and the pressure transducer, and a data acquisition and processing system capable of receiving conductance data from the detector and calculating a balloon cross-sectional area based upon a detected conductance of a fluid within the balloon from the detector, a known conductivity of the fluid, and a known distance between two detection electrodes of the detector.

In at least one embodiment of a device for obtaining measurements within a luminal organ of the present disclosure, the device comprises an elongated body and at least one sizing finger hingedly connected to the elongated body, the at least one sizing finger configured to move from a first position to a second position by way of adjustment of a control wire coupled thereto. In another embodiment, the at least one sizing finger comprises two or more sizing fingers.

In at least one embodiment of a device for obtaining measurements within a luminal organ of the present disclosure, the device comprises an elongated body and at least one sizing finger coupled thereto, the at least one sizing finger configured to move from a first position to a second position by way of adjustment of a sliding shaft within a lumen defined within the device. In an additional embodiment, the at least one sizing finger comprises two or more sizing fingers. In another embodiment, the device further comprises one or more electrodes coupled to a portion of the device. In yet another embodiment, the device further comprises one or more piezoelectric sensors coupled to a portion of the device. In an additional embodiment, the device further comprises one or more coils coupled to a portion of the device.

In at least one embodiment of a device for obtaining measurements within a luminal organ of the present disclosure, the device comprises an elongated body and a plurality of linear extensions extending therefrom at a distal end of the elongated body, at least one of the plurality of linear extensions comprising two or more electrodes coupled thereto. In an additional embodiment, the device further comprises a push/pull wire coupled to at least one of the plurality of linear extensions, wherein movement of the push/pull wire causes movement of the at least one of the plurality of linear extensions. In yet an additional embodiment, the device further comprises one or more piezoelectric sensors coupled to a portion of the device.

In at least one embodiment of a device for obtaining measurements within a luminal organ of the present disclosure, the device comprises an elongated body having a distal region forming a circular region, wherein at least two electrodes are present within the circular region.

In at least one embodiment of a device for obtaining measurements within a luminal organ of the present disclosure, the device comprises an elongated body and a plurality of curved arms forming a bulbous configuration at the end of the elongated body, and wherein at least two electrodes are present within the bulbous configuration.

In at least one embodiment of a device for obtaining measurements within a luminal organ of the present disclosure, the device comprises an elongated body having a balloon coupled thereto, with more than four electrodes positioned within the balloon, wherein two or more conductance measurements can be obtained between different electrode pairs of the more than four electrodes.

In at least one embodiment of a device for obtaining measurements within a luminal organ of the present disclosure, the device comprises an elongated body, and at least one sizing finger positioned at a distal end of the elongated body, the at least one sizing finger configured to move from a first position to a second position by way of adjustment of at least one movable device coupled thereto, wherein a dimensional measurement within the luminal organ can be determined based upon the first position and the second position. In at least one embodiment, the at least one sizing finger is hingedly coupled to the elongated body. In at least one embodiment, the at least one movable device comprises a control wire extending between the at least one sizing finger and a proximal end of the elongated body. In at least one embodiment, the at least one sizing finger comprises a first sizing finger and a second sizing finger, wherein the at least one movable device comprises a first control wire coupled to the first sizing finger and a second control wire coupled to the second sizing finger, wherein the first control wire is configured to move independently from the second control wire. In at least one embodiment, the device further comprises at least one force measuring apparatus coupled to the at least one sizing finger, the at least one force measuring apparatus configured to quantify mechanical resistance of the at least one finger relative to a wall of the luminal organ.

In at least one embodiment of a device for obtaining measurements within a luminal organ of the present disclosure, the at least one sizing finger comprises two or more sizing fingers. In at least one embodiment, the at least one movable device comprises an inner shaft positioned within the elongated body and extending from and coupled to the at least one sizing finger to a proximal end of the elongated body, and wherein the at least one sizing finger configured to move from the first position to the second position by way of movement of the inner shaft. In at least one embodiment, the at least one sizing finger comprises a first sizing finger and a second sizing finger, and wherein the device further comprises a first electrode positioned upon the first sizing finger and a second electrode positioned upon the second sizing finger.

In at least one embodiment of a device for obtaining measurements within a luminal organ of the present disclosure, the device further comprises a third electrode and a fourth electrode positioned along the elongated body. In at least one embodiment, a first difference in voltage obtained using the first electrode and the second electrode can be obtained using the device, whereby a second difference in voltage obtained using the third electrode and the fourth electrode can be obtained using the device, the first voltage difference and the second voltage difference being a function of at least one distance between two or more of the first electrode, the second electrode, the third electrode, and/or the fourth electrode. In at least one embodiment, the device further comprises a first coil positioned upon one of the first sizing finger or the second sizing finger, the first coil configured to generate a magnetic field detectable using at least one of the first electrode, the second electrode, or an additional electrode positioned upon a portion of the device. In at least one embodiment, the device further comprises a first piezoelectric sensor positioned upon the first sizing finger and a second piezoelectric sensor positioned upon the second sizing finger, the first piezoelectric sensor configured to generate an ultrasonic wave detectable by the second piezoelectric sensor, whereby a transmission time of the ultrasonic wave is indicative of a distance between the first piezoelectric sensor and the second piezoelectric sensor, which is indicative of the dimensional measurement. In at least one embodiment, the third electrode and the fourth electrode are configured to detect an electric field within the luminal organ to generate impedance data, wherein the impedance data and a known distance between the third electrode and the fourth electrode are used to determine the dimensional measurement.

In at least one embodiment of a device for obtaining measurements within a luminal organ of the present disclosure, the device comprises an elongated body, at least one sizing finger positioned at a distal end of the elongated body, the at least one sizing finger configured to move from a first position to a second position by way of adjustment of at least one movable device coupled thereto, the movable device selected from the group consisting of a control wire extending between the at least one sizing finger and a proximal end of the elongated body and an inner shaft positioned within the elongated body and extending from and coupled to the at least one sizing finger to the proximal end of the elongated body, and wherein a dimensional measurement within the luminal organ can be determined based upon the first position and the second position of the at least one sizing finger, the dimensional measurement selected from the group consisting of a cross-sectional area of the luminal organ, a valve aperture dimensional measurement, and a valve annulus dimensional measurement. In at least one embodiment, the at least one sizing finger comprises a first sizing finger and a second sizing finger, and wherein the device further comprises a first electrode positioned upon the first sizing finger and a second electrode positioned upon the second sizing finger, whereby a first difference in voltage obtained using the first electrode and the second electrode can be obtained using the device.

In at least one embodiment of a method for obtaining measurements within a luminal organ of the present disclosure, the method comprises the steps of positioning at least part of a device within a luminal organ, the device comprising an elongated body, and at least one sizing finger positioned at a distal end of the elongated body, the at least one sizing finger configured to move from a first position to a second position by way of adjustment of at least one movable device coupled thereto, moving the at least one movable device in a first direction to cause the at least one sizing finger to move from the first position to the second position, and determining a dimensional measurement within the luminal organ based upon the first position and the second position. In at least one embodiment, the determining step includes the step of identifying a distance of movement of the at least one movable device based upon indicia of the at least one movable device. In at least one embodiment, the at least one sizing finger comprises a first sizing finger and a second sizing finger, wherein the device further comprises a first electrode positioned upon the first sizing finger and a second electrode positioned upon the second sizing finger, and wherein the determining step includes the step of obtaining a first voltage measurement between the first electrode and the second electrode. In at least one embodiment, the device further comprises a third electrode and a fourth electrode positioned along the elongated body, and wherein the determining step includes the step of obtaining a second voltage measurement between the third electrode and the fourth electrode. In at least one embodiment, the moving step is performed to cause the at least one sizing finger to move from the first position of being relatively aligned with the elongated body to the second position of extending from the elongated body so that at least part of the at least one sizing finger contacts a wall of the luminal organ. In at least one embodiment, the at least one sizing finger comprises a first sizing finger and a second sizing finger each coupled to the movable device, wherein the moving step is performed to cause the first sizing finger and the second sizing finger to move from the first position of being within the elongated body to the second position of extending from the elongated body so that at least part of each of the first sizing finger and the second sizing finger contact a wall of the luminal organ.

BRIEF DESCRIPTION OF THE DRAWINGS

FIG. 1A shows a balloon catheter having impedance measuring electrodes supported in front of the stenting balloon, according to an embodiment of the present disclosure;

FIG. 1B shows a balloon catheter having impedance measuring electrodes within and in front of the balloon, according to an embodiment of the present disclosure;

FIG. 1C shows a catheter having an ultrasound transducer within and in front of balloon, according to an embodiment of the present disclosure;

FIG. 1D shows a catheter without a stenting balloon, according to an embodiment of the present disclosure;

FIG. 1E shows a guide catheter with wire and impedance electrodes, according to an embodiment of the present disclosure;

FIG. 1F shows a catheter with multiple detection electrodes, according to an embodiment of the present disclosure;

FIG. 15A shows a side view of at least part of a sizing device, according to an exemplary embodiment of the present disclosure;

FIG. 15B shows a front end view of at least part of a sizing device, according to an exemplary embodiment of the present disclosure;

FIG. 15C shows a side view of at least part of a sizing device, according to an exemplary embodiment of the present disclosure;

FIG. 15D shows a front end view of at least part of a sizing device, according to an exemplary embodiment of the present disclosure;

DETAILED DESCRIPTION

Figure 2B:
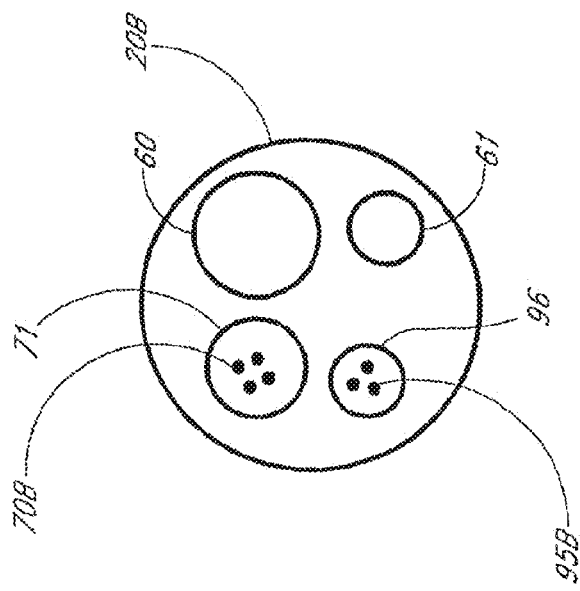
FIG. 2B shows a catheter in cross-section proximal to the location of the sensors showing the leads run in separate lumens, according to an embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

This present disclosure makes accurate measures of the luminal cross-sectional area of organ stenosis within acceptable limits to enable accurate and scientific stent sizing and placement in order to improve clinical outcomes by avoiding under or over deployment and under or over sizing of a stent which can cause acute closure or in-stent re-stenosis. In one embodiment, an angioplasty or stent balloon includes impedance electrodes supported by the catheter in front of the balloon. These electrodes enable the immediate measurement of the cross-sectional area of the vessel during the balloon advancement. This provides a direct measurement of non-stenosed area and allows the selection of the appropriate stent size. In one approach, error due to the loss of current in the wall of the organ and surrounding tissue is corrected by injection of two solutions of NaCl or other solutions with known conductivities. In another embodiment impedance electrodes are located in the center of the balloon in order to deploy the stent to the desired cross-sectional area. These embodiments and procedures substantially improve the accuracy of stenting and the outcome and reduce the cost.

Other embodiments make diagnosis of valve stenosis more accurate and more scientific by providing a direct accurate measurement of cross-sectional area of the valve annulus, independent of the flow conditions through the valve. Other embodiments improve evaluation of cross-sectional area and flow in organs like the gastrointestinal tract and the urinary tract.

Embodiments of the present disclosure overcome the problems associated with determination of the size (cross-sectional area) of luminal organs, such as, for example, in the coronary arteries, carotid, femoral, renal and iliac arteries, aorta, gastrointestinal tract, urethra and ureter, Embodiments also provide methods for registration of acute changes in wall conductance, such as, for example, due to edema or acute damage to the tissue, and for detection of muscle spasms/contractions.

As described below, in one preferred embodiment, there is provided an angioplasty catheter with impedance electrodes near the distal end 19 of the catheter (i.e., in front of the balloon) for immediate measurement of the cross-sectional area of a vessel lumen during balloon advancement. This catheter includes electrodes for accurate detection of organ luminal cross-sectional area and ports for pressure gradient measurements. Hence, it is not necessary to change catheters such as with the current use of intravascular ultrasound. In one preferred embodiment, the catheter provides direct measurement of the non-stenosed area, thereby allowing the selection of an appropriately sized stent. In another embodiment, additional impedance electrodes may be incorporated in the center of the balloon on the catheter in order to deploy the stent to the desired cross-sectional area. The procedures described herein substantially improve the accuracy of stenting and improve the cost and outcome as well.

In another embodiment, the impedance electrodes are embedded within a catheter to measure the valve area directly and independent of cardiac output or pressure drop and therefore minimize errors in the measurement of valve area. Hence, measurements of area are direct and not based on calculations with underlying assumptions. In another embodiment, pressure sensors can be mounted proximal and distal to the impedance electrodes to provide simultaneous pressure gradient recording.

Catheter

We designed and build the impedance or conductance catheters illustrated in FIGS. 1A-1F. With reference to the exemplary embodiment shown in FIG. 1A, four wires were threaded through one of the 2 lumens of a 4 Fr catheter. Here, electrodes 26 and 28, are spaced 1 mm apart and form the inner (detection) electrodes. Electrodes 25 and 27 are spaced 4-5 mm from either side of the inner electrodes and form the outer (excitation) electrodes.

In one approach, dimensions of a catheter to be used for any given application depend on the optimization of the potential field using finite element analysis described below. For small organs or in pediatric patients the diameter of the catheter may be as small as 0.3 mm. In large organs the diameter may be significantly larger depending on the results of the optimization based on finite element analysis. The balloon size will typically be sized according to the preferred dimension of the organ after the distension. The balloon may be made of materials, such as, for example, polyethylene, latex, polyestherurethane, or combinations thereof. The thickness of the balloon will typically be on the order of a few microns. The catheter will typically be made of PVC or polyethylene, though other materials may equally well be used. The excitation and detection electrodes typically surround the catheter as ring electrodes but they may also be point electrodes or have other suitable configurations. These electrodes may be made of any conductive material, preferably of platinum iridium or a carbon-coasted surface to avoid fibrin deposits. In the preferred embodiment, the detection electrodes are spaced with 0.5-1 mm between them and with a distance between 4-7 mm to the excitation electrodes on small catheters. The dimensions of the catheter selected for a treatment depend on the size of the vessel and are preferably determined in part on the results of finite element analysis, described below. On large catheters, for use in larger vessels and other visceral hollow organs, the electrode distances may be larger.

Referring to FIGS. 1A, 1B, 1C and 1D, several embodiments of the catheters are illustrated. The catheters shown contain to a varying degree different electrodes, number and optional balloon(s). With reference to the embodiment shown in FIG. 1A, there is shown an impedance catheter 20 with 4 electrodes 25, 26, 27 and 28 placed close to the tip 19 of the catheter. Proximal to these electrodes is an angiography or stenting balloon 30 capable of being used for treating stenosis. Electrodes 25 and 27 are excitation electrodes, while electrodes 26 and 28 are detection electrodes, which allow measurement of cross-sectional area during advancement of the catheter, as described in further detail below. The portion of the catheter 20 within balloon 30 includes an infusion port 35 and a pressure port 36.

The catheter 20 may also advantageously include several miniature pressure transducers (not shown) carried by the catheter or pressure ports for determining the pressure gradient proximal at the site where the cross-sectional area is measured. The pressure is preferably measured inside the balloon and proximal, distal to and at the location of the cross-sectional area measurement, and locations proximal and distal thereto, thereby enabling the measurement of pressure recordings at the site of stenosis and also the measurement of pressure-difference along or near the stenosis. In one embodiment, shown in FIG. 1A, Catheter 20 advantageously includes pressure port 90 and pressure port 91 proximal to or at the site of the cross-sectional measurement for evaluation of pressure gradients. As described below with reference to FIGS. 2A, 2B and 3, in one embodiment, the pressure ports are connected by respective conduits in the catheter 20 to pressure sensors in the data acquisition system 100. Such pressure sensors are well known in the art and include, for example, fiber-optic systems, miniature strain gauges, and perfused low-compliance manometry.

In one embodiment, a fluid-filled silastic pressure-monitoring catheter is connected to a pressure transducer. Luminal pressure can be monitored by a low compliance external pressure transducer coupled to the infusion channel of the catheter. Pressure transducer calibration was carried out by applying 0 and 100 mmHg of pressure by means of a hydrostatic column.

In one embodiment, shown in FIG. 1B, the catheter 39 includes another set of excitation electrodes 40, 41 and detection electrodes 42, 43 located inside the angioplastic or stenting balloon 30 for accurate determination of the balloon cross-sectional area during angioplasty or stent deployment. These electrodes are in addition to electrodes 25, 26, 27 and 28.

In one embodiment, the cross-sectional area may be measured using a two-electrode system. In another embodiment, illustrated in FIG. 1F, several cross-sectional areas can be measured using an array of 5 or more electrodes. Here, the excitation electrodes 51, 52, are used to generate the current while detection electrodes 53, 54, 55, 56 and 57 are used to detect the current at their respective sites.

The tip of the catheter can be straight, curved or with an angle to facilitate insertion into the coronary arteries or other lumens, such as, for example, the biliary tract. The distance between the balloon and the electrodes is usually small, in the 0.5-2 cm range but can be closer or further away, depending on the particular application or treatment involved.

In another embodiment, shown in FIG. 1C the catheter 21 has one or more imaging or recording device, such as, for example, ultrasound transducers 50 for cross-sectional area and wall thickness measurements. As shown in this embodiment, the transducers 50 are located near the distal tip 19 of the catheter 21.

FIG. 1D shows an embodiment of the impedance catheter 22 without an angioplastic or stenting balloon. This catheter also possesses an infusion or injection port 35 located proximal relative to the excitation electrode 25 and pressure port 36.

With reference to the embodiment shown in FIG. 1E, the electrodes 25, 26, 27, 28 can also be built onto a wire 18, such as, for example, a pressure wire, and inserted through a guide catheter 23 where the infusion of bolus can be made through the lumen of the guide catheter 37.

With reference to the embodiments shown in FIGS. 1A, 1B, 1C, 1D, 1E and 1F, the impedance catheter advantageously includes optional ports 35, 36, 37 for suction of contents of the organ or infusion of fluid. The suction/infusion port 35, 36, 37 can be placed as shown with the balloon or elsewhere both proximal or distal to the balloon on the catheter. The fluid inside the balloon can be any biologically compatible conducting fluid. The fluid to inject through the infusion port or ports can be any biologically compatible fluid but the conductivity of the fluid is selected to be different from that of blood (e.g., NaCl).

In another embodiment (not illustrated), the catheter contains an extra channel for insertion of a guide wire to stiffen the flexible catheter during the insertion or data recording. In yet another embodiment (not illustrated), the catheter includes a sensor for measurement of the flow of fluid in the body organ.

System for Determining Cross-Sectional Area and Pressure Gradient

The operation of the impedance catheter 20 is as follows: With reference to the embodiment shown in FIG. 1A for electrodes 25, 26, 27, 28, conductance of current flow through the organ lumen and organ wall and surrounding tissue is parallel; i.e., $$G(z, t) = \frac{CSA(z, t) \cdot C_b}{L} + G_p(z, t) \quad [1a]$$

where $G_p(z,t)$ is the effective conductance of the structure outside the bodily fluid (organ wall and surrounding tissue), and $C_b$ is the specific electrical conductivity of the bodily fluid which for blood generally depends on the temperature, hematocrit and orientation and deformation of blood cells and L is the distance between the detection electrodes. Equation[1] can be rearranged to solve for cross sectional area CSA(t), with a correction factor, α, if the electric field is non-homogeneous, as $$CSA(z, t) = \frac{L}{\alpha C_b}[G(z, t) - G_p(z, t)] \quad [1b]$$

where α would be equal to 1 if the field were completely homogeneous. The parallel conductance, $G_p$, is an offset error that results from current leakage. $G_p$ would equal 0 if all of the current were confined to the blood and hence would correspond to the cylindrical model given by Equation[10]. In one approach, finite element analysis is used to properly design the spacing between detection and excitation electrodes relative to the dimensions of the vessel to provide a nearly homogenous field such that a can be considered equal to 1. Our simulations show that a homogenous or substantially homogenous field is provided by (1) the placement of detection electrodes substantially equidistant from the excitation electrodes and (2) maintaining the distance between the detection and excitation electrodes substantially comparable to the vessel diameter. In one approach, a homogeneous field is achieved by taking steps (1) and/or (2) described above so that α is equals 1 in the foregoing analysis.

At any given position, z, along the long axis of organ and at any given time, t, in the cardiac cycle, $G_p$ is a constant. Hence, two injections of different concentrations and/or conductivities of NaCl solution give rise to two Equations:

$$C_1 \cdot CSA(z,t) + L \cdot G_p(z,t) = L \cdot G_1(z,t) \quad [2]$$

and $$C_2 \cdot CSA(z,t) + L \cdot G_p(z,t) = L \cdot G_2(z,t) \quad [3]$$

which can be solved simultaneously for CSA and $G_p$ as $$CSA(z, t) = L\frac{[G_2(z, t) - G_1(z, t)]}{[C_2 - C_1]} \quad \text{and} \quad [4]$$

$$G_p(z, t) = \frac{[C_2 \cdot G_1(z, t) - C_1 \cdot G_2(z, t)]}{[C_2 - C_1]} \quad [5]$$

where subscript "1" and subscript "2" designate any two injections of different NaCl concentrations and/or conductivities. For each injection k, $C_k$ gives rise to $G_k$ which is measured as the ratio of the root mean square of the current divided by the root mean square of the voltage. The $C_k$ is typically determined through in vitro calibration for the various NaCl concentrations and/or conductivities. The concentration of NaCl used is typically on the order of 0.45 to 1.8%. The volume of NaCl solution is typically about 5 ml, but sufficient to displace the entire local vascular blood volume momentarily. The values of CSA(t) and $G_p$(t) can be determined at end-diastole or end-systole (i.e., the minimum and maximum values) or the mean thereof.

Once the CSA and $G_p$ of the vessel are determined according to the above embodiment, rearrangement of Equation[1] allows the calculation of the specific electrical conductivity of blood in the presence of blood flow as $$C_b = \frac{L}{CSA(z, t)}[G(z, t) - G_p(z, t)] \quad [6]$$

In this way, Equation [1b] can be used to calculate the CSA continuously (temporal variation as for example through the cardiac cycle) in the presence of blood.

In one approach, a pull or push through is used to reconstruct the vessel along its length. During a long injection (e.g., 10-15 s), the catheter can be pulled back or pushed forward at constant velocity U. Equation [1b] can be expressed as $$CSA(U \cdot t, t) = \frac{L}{C_b}[G(U \cdot t, t) - G_p(U \cdot (t, t)]\quad[7]$$

where the axial position, z, is the product of catheter velocity, U, and time, t; i.e., z=U·t.

For the two injections, denoted by subscript "1" and subscript "2", respectively, we can consider different time points T1, T2, etc. such that Equation[7] can be written as $$CSA_1(U \cdot T_1, t) = \frac{L}{C_1}[G_1(U \cdot T_1, t) - G_{p1}(U \cdot T_1, t)]\quad[8a]$$

$$CSA_1(U \cdot T_1, t) = \frac{L}{C_2}[G_2(U \cdot T_1, t) - G_{p1}(U \cdot T_1, t)]\quad[8b]$$

and $$CSA_2(U \cdot T_2, t) = \frac{L}{C_1}[G_1(U \cdot T_2, t) - G_{p2}(U \cdot T_2, t)]\quad[9a]$$

$$CSA_2(U \cdot T_2, t) = \frac{L}{C_2}[G_2(U \cdot T_2, t) - G_{p2}(U \cdot T_2, t)]\quad[9b]$$

and so on. Each set of Equations [8a], [8b] and [9a], [9b], etc. can be solved for $CSA_1$, $G_{p1}$ and $CSA_2$, $G_{p2}$, respectively. Hence, we can measure the CSA at various time intervals and hence of different positions along the vessel to reconstruct the length of the vessel. In one embodiment, the data on the CSA and parallel conductance as a function of longitudinal position along the vessel can be exported from an electronic spreadsheet, such as, for example, an Excel file, to AutoCAD where the software uses the coordinates to render a 3-Dimensional vessel on the monitor.

For example, in one exemplary approach, the pull back reconstruction was made during a long injection where the catheter was pulled back at constant rate by hand. The catheter was marked along its length such that the pull back was made at 2 mm/sec. Hence, during a 10 second injection, the catheter was pulled back about 2 cm. The data was continuously measured and analyzed at every two second interval; i.e., at every 4 mm. Hence, six different measurements of CSA and $G_p$ were made which were used to reconstruction the CSA and $G_p$ along the length of the 2 cm segment.

Operation of the Impedance Catheter 39:

With reference to the embodiment shown in FIG. 1B, the voltage difference between the detection electrodes 42 and 43 depends on the magnitude of the current (I) multiplied by the distance (D) between the detection electrodes and divided by the conductivity (C) of the fluid and the cross-sectional area (CSA) of the artery or other organs into which the catheter is introduced. Since the current (I), the distance (L) and the conductivity (C) normally can be regarded as calibration constants, an inverse relationship exists between the voltage difference and the CSA as shown by the following Equations:

$$\Delta V = \frac{I \cdot L}{C \cdot CSA} \text{ or }\quad[10a]$$

$$CSA = \frac{G \cdot L}{C}\quad[10b]$$

where G is conductance expressed as the ratio of current to voltage (I/ΔV). Equation[10] is identical to Equation [1b] if we neglect the parallel conductance through the vessel wall and surrounding tissue because the balloon material acts as an insulator. This is the cylindrical model on which the conductance method is used.

As described below with reference to FIGS. 2A, 2B, 3, 4 and 5, the excitation and detection electrodes are electrically connected to electrically conductive leads in the catheter for connecting the electrodes to the data acquisition system 100.

Figure 2A:
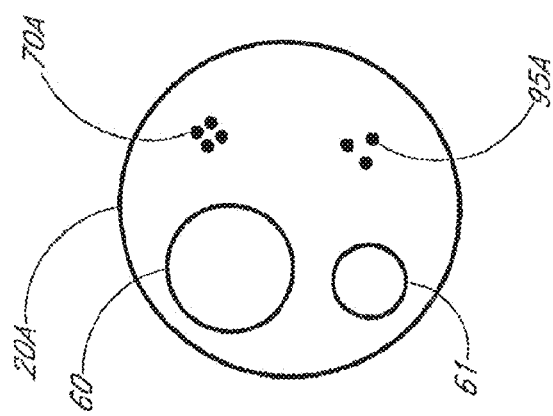
FIG. 2A shows a catheter in cross-section proximal to the location of the sensors showing the leads embedded in the material of the probe, according to an embodiment of the present disclosure.

FIGS. 2A and 2B illustrate two embodiments 20A and 20B of the catheter in cross-section. Each embodiment has a lumen 60 for inflating and deflating the balloon and a lumen 61 for suction and infusion. The sizes of these lumens can vary in size. The impedance electrode electrical leads 70A are embedded in the material of the catheter in the embodiment in FIG. 2A, whereas the electrode electrical leads 70B are tunneled through a lumen 71 formed within the body of catheter 70B in FIG. 2B.

Pressure conduits for perfusion manometry connect the pressure ports 90, 91 to transducers included in the data acquisition system 100. As shown in FIG. 2A pressure conduits 95A may be formed in 20A. In another embodiment, shown in FIG. 2B, pressure conduits 95B constitute individual conduits within a tunnel 96 formed in catheter 20B. In the embodiment described above where miniature pressure transducers are carried by the catheter, electrical conductors will be substituted for these pressure conduits.

Figure 3:
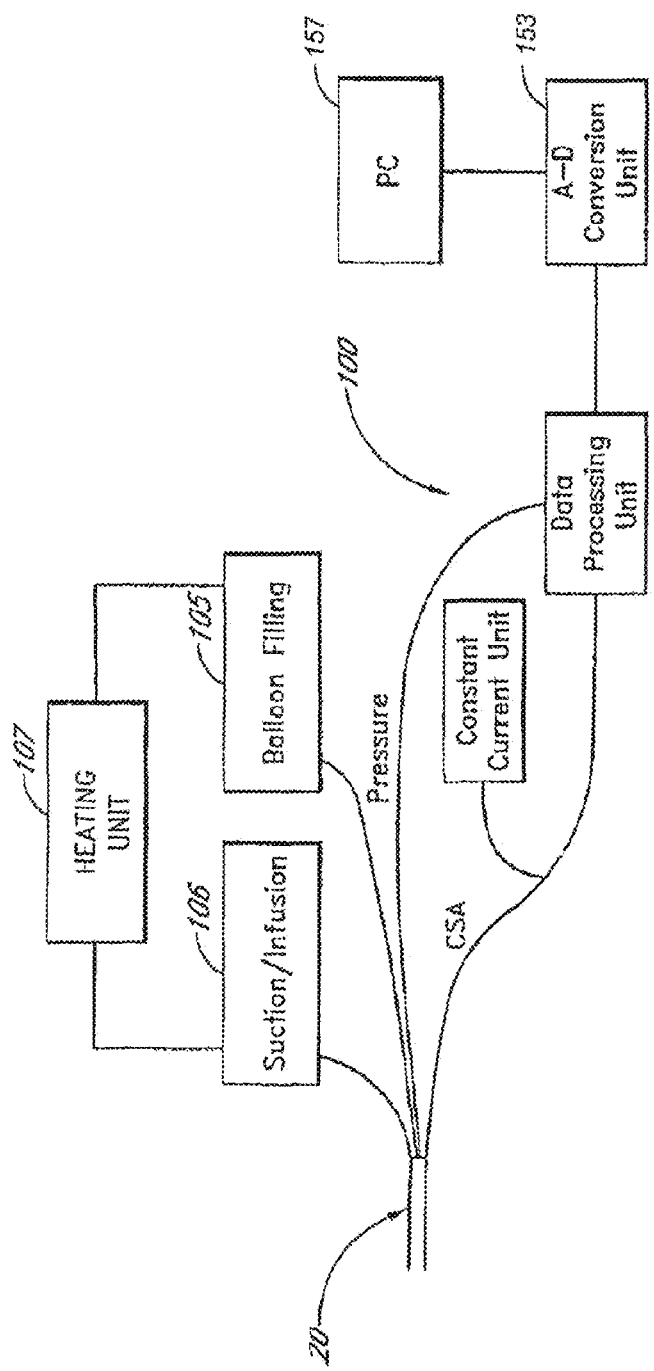
FIG. 3 is a schematic of one embodiment of the system showing a catheter carrying impedance measuring electrodes connected to the data acquisition equipment and excitation unit for the cross-sectional area measurement, according to an embodiment of the present disclosure.

With reference to FIG. 3, in one embodiment, the catheter 20 connects to a data acquisition system 100, to a manual or automatic system 105 for distension of the balloon and to a system 106 for infusion of fluid or suction of blood. The fluid will be heated to 37-39° or equivalent to body temperature with heating unit 107. The impedance planimetry system typically includes a current unit, amplifiers and signal conditioners. The pressure system typically includes amplifiers and signal conditioners. The system can optionally contain signal conditioning equipment for recording of fluid flow in the organ.

In one preferred embodiment, the system is pre-calibrated and the probe is available in a package. Here, the package also preferably contains sterile syringes with the fluids to be injected. The syringes are attached to the machine and after heating of the fluid by the machine and placement of the probe in the organ of interest, the user presses a button that initiates the injection with subsequent computation of the desired parameters. The CSA and parallel conductance and other relevant measures such as distensibility, tension, etc. will typically appear on the display panel in the PC module 160. Here, the user can then remove the stenosis by distension or by placement of a stent.

If more than one CSA is measured, the system can contain a multiplexer unit or a switch between CSA channels. In one embodiment, each CSA measurement will be through separate amplifier units. The same may account for the pressure channels.

In one embodiment, the impedance and pressure data are analog signals which are converted by analog-to-digital converters 150 and transmitted to a computer 160 for on-line display, on-line analysis and storage. In another embodiment, all data handling is done on an entirely analog basis. The analysis advantageously includes software programs for reducing the error due to conductance of current in the organ wall and surrounding tissue and for displaying the 2D or 3D-geometry of the CSA distribution along the length of the vessel along with the pressure gradient. In one embodiment of the software, a finite element approach or a finite difference approach is used to derive the CSA of the organ stenosis taking parameters such as conductivities of the fluid in the organ and of the organ wall and surrounding tissue into consideration. In another embodiment, simpler circuits are used; e.g., based on making two or more injections of different NaCl solutions to vary the resistivity of fluid in the vessel and solving the two simultaneous Equations [2] and [3] for the CSA and parallel conductance (Equations [4] and [5], respectively). In another embodiment, the software contains the code for reducing the error in luminal CSA measurement by analyzing signals during interventions such as infusion of a fluid into the organ or by changing the amplitude or frequency of the current from the current amplifier, which may be a constant current amplifier. The software chosen for a particular application, preferably allows computation of the CSA with only a small error instantly or within acceptable time during the medical procedure.

In one approach, the wall thickness is determined from the parallel conductance for those organs that are surrounded by air or non-conducting tissue. In such cases, the parallel conductance is equal to $$G_p = \frac{CSA_w \cdot C_w}{L} \quad [11a]$$

where $CSA_w$ is the wall area of the organ and $C_w$ is the electrical conductivity through the wall. This Equation can be solved for the wall $CSA_w$ as $$CSA_w = \frac{G_p \cdot L}{C_w} \quad [11b]$$

For a cylindrical organ, the wall thickness, h, can be expressed as $$h = \frac{CSA_w}{\pi D} \quad [12]$$

where D is the diameter of the vessel which can be determined from the circular CSA ($D = [4CSA/\pi]^{1/2}$).

When the CSA, pressure, wall thickness, and flow data are determined according to the embodiments outlined above, it is possible to compute the compliance (e.g., $\Delta CSA/\Delta P$), tension (e.g., $P \cdot r$, where P and r are the intraluminal pressure and radius of a cylindrical organ), stress (e.g., $P \cdot r/h$ where h is the wall thickness of the cylindrical organ), strain (e.g., $(C-C_d)/C_d$ where C is the inner circumference and $C_d$ is the circumference in diastole) and wall shear stress (e.g., $4 \mu Q/r^3$ where $\mu$, Q and r are the fluid viscosity, flow rate and radius of the cylindrical organ for a fully developed flow). These quantities can be used in assessing the mechanical characteristics of the system in health and disease.

Method

In one approach, luminal cross-sectional area is measured by introducing a catheter from an exteriorly accessible opening (e.g., mouth, nose or anus for GI applications; or e.g., mouth or nose for airway applications) into the hollow system or targeted luminal organ. For cardiovascular applications, the catheter can be inserted into the organs in various ways; e.g., similar to conventional angioplasty. In one embodiment, an 18 gauge needle is inserted into the femoral artery followed by an introducer. A guide wire is then inserted into the introducer and advanced into the lumen of the femoral artery. A 4 or 5 Fr conductance catheter is then inserted into the femoral artery via wire and the wire is subsequently retracted. The catheter tip containing the conductance electrodes can then be advanced to the region of interest by use of x-ray (i.e., fluoroscopy). In another approach, this methodology is used on small to medium size vessels (e.g., femoral, coronary, carotid, iliac arteries, etc.).

In one approach, a minimum of two injections (with different concentrations and/or conductivities of NaCl) are required to solve for the two unknowns, CSA and $G_p$. In another approach, three injections will yield three set of values for CSA and $G_p$ (although not necessarily linearly independent), while four injections would yield six set of values. In one approach, at least two solutions (e.g., 0.5% and 1.5% NaCl solutions) are injected in the targeted luminal organ or vessel. Our studies indicate that an infusion rate of approximately 1 ml/s for a five second interval is sufficient to displace the blood volume and results in a local pressure increase of less than 10 mmHg in the coronary artery. This pressure change depends on the injection rate which should be comparable to the organ flow rate.

In one preferred approach, involving the application of Equations [4] and [5], the vessel is under identical or very similar conditions during the two injections. Hence, variables, such as, for example, the infusion rate, bolus temperature, etc., are similar for the two injections. Typically, a short time interval is to be allowed (1-2 minute period) between the two injections to permit the vessel to return to homeostatic state. This can be determined from the baseline conductance as shown in FIG. 4 or 5. The parallel conductance is preferably the same or very similar during the two injections. In one approach, dextran, albumin or another large molecular weight molecule can be added to the NaCl solutions to maintain the colloid osmotic pressure of the solution to reduce or prevent fluid or ion exchange through the vessel wall.

In one approach, the NaCl solution is heated to body temperature prior to injection since the conductivity of current is temperature dependent. In another approach, the injected bolus is at room temperature, but a temperature correction is made since the conductivity is related to temperature in a linear fashion.

In one approach, a sheath is inserted either through the femoral or carotid artery in the direction of flow. To access the lower anterior descending (LAD) artery, the sheath is inserted through the ascending aorta. For the carotid artery, where the diameter is typically on the order of 5-5.5 mm, a catheter having a diameter of 1.9 mm can be used, as determined from finite element analysis, discussed further below. For the femoral and coronary arteries, where the diameter is typically in the range from 3.5-4 mm, so a catheter of about 0.8 mm diameter would be appropriate. The catheter can be inserted into the femoral, carotid or LAD artery through a sheath appropriate for the particular treatment. Measurements for all three vessels can be made similarly.

Described here are the protocol and results for one exemplary approach that is generally applicable to most arterial vessels. The conductance catheter was inserted through the sheath for a particular vessel of interest. A baseline reading of voltage was continuously recorded. Two containers containing 0.5% and 1.5% NaCl were placed in temperature bath and maintained at 37°. A 5-10 ml injection of 1.5% NaCl was made over a 5 second interval. The detection voltage was continuously recorded over a 10 second interval during the 5 second injection. Several minutes later, a similar volume of 1.5% NaCl solution was injected at a similar rate. The data was again recorded. Matlab was used to analyze the data including filtering with high pass and with low cut off frequency (1200 Hz). The data was displayed using Matlab and the mean of the voltage signal during the passage of each respective solution was recorded. The corresponding currents were also measured to yield the conductance (G=I/V). The conductivity of each solution was calibrated with six different tubes of known CSA at body temperature. A model using Equation[10] was fitted to the data to calculate conductivity C. The analysis was carried out in SPSS using the non-linear regression fit. Given C and G for each of the two injections, an excel sheet file was formatted to calculate the CSA and $G_p$ as per Equations [4] and [5], respectively. These measurements were repeated several times to determine the reproducibility of the technique. The reproducibility of the data was within 5%. Ultrasound (US) was used to measure the diameter of the vessel simultaneous with our conductance measurements. The detection electrodes were visualized with US and the diameter measurements was made at the center of the detection electrodes. The maximum differences between the conductance and US measurements were within 10%.

FIGS. 4A, 4B, 5A and 5B illustrate voltage measurements in the blood stream in the left carotid artery. Here, the data acquisition had a sampling frequency of 75 KHz, with two channels—the current injected and the detected voltage, respectively. The current injected has a frequency of 5 KH, so the voltage detected, modulated in amplitude by the impedance changing through the bolus injection will have a spectrum in the vicinity of 5 KHz.

Figure 4A:
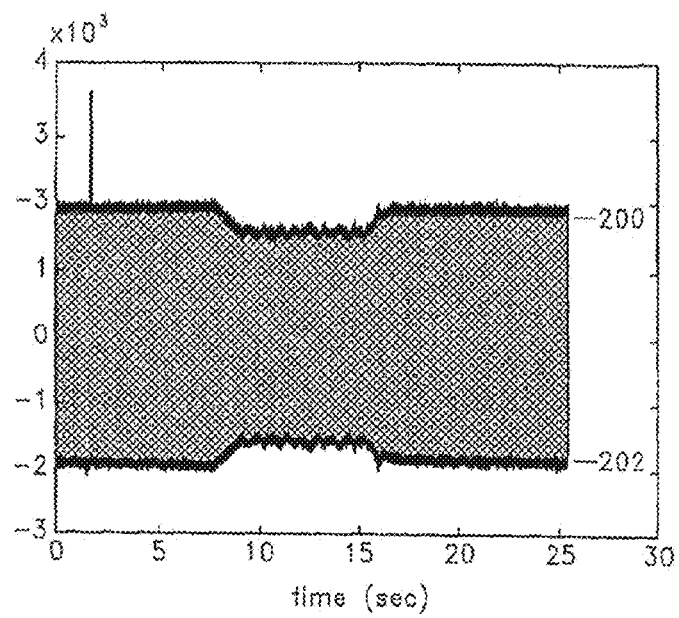
FIG. 4A shows the detected filtered voltage drop as measured in the blood stream before and after injection of 1.5% NaCl solution, according to an embodiment of the present disclosure.
Figure 4B:
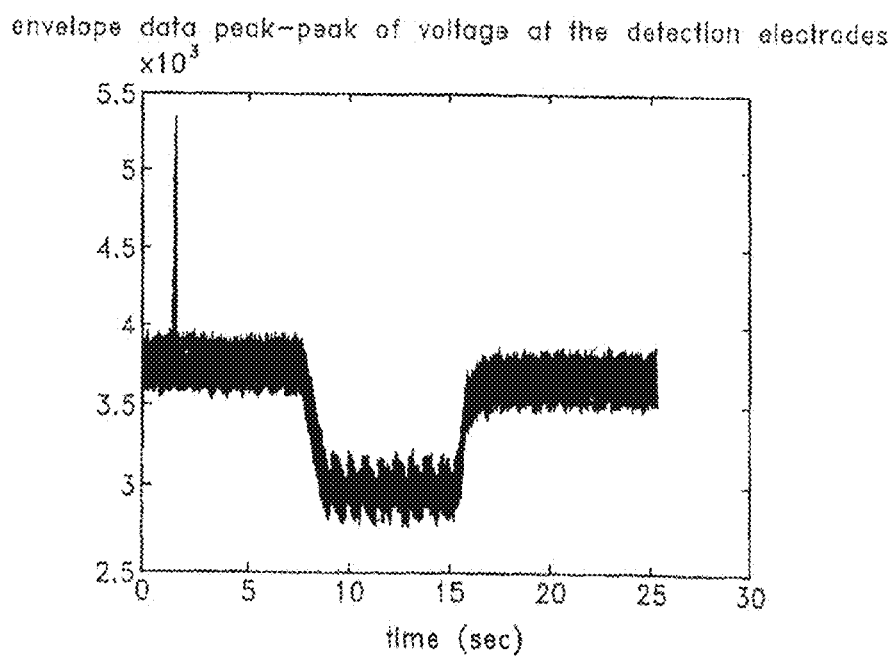
FIG. 4B shows the peak-to-peak envelope of the detected voltage shown in FIG. 4A, according to an embodiment of the present disclosure.
Figure 5A:
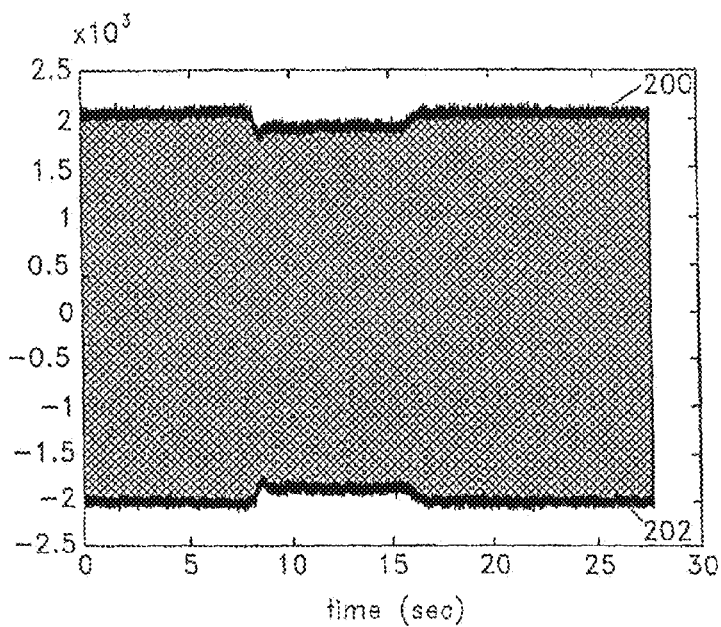
FIG. 5A shows the detected filtered voltage drop as measured in the blood stream before and after injection of 0.5% NaCl solution, according to an embodiment of the present disclosure.
Figure 5B:
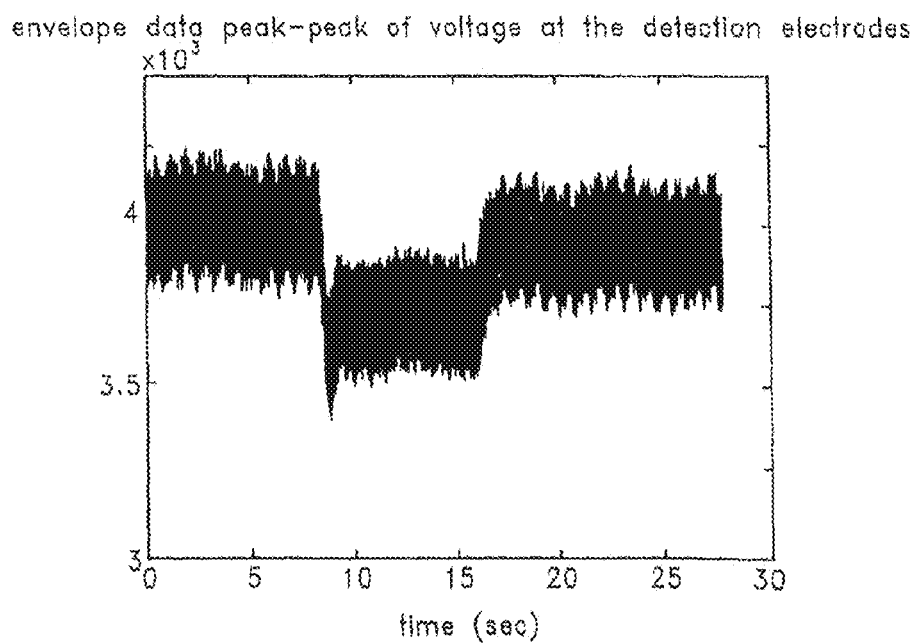
FIG. 5B shows the peak-to-peak envelope of the detected voltage shown in FIG. 5A, according to an embodiment of the present disclosure.

With reference to FIG. 4A there is shown a signal processed with a high pass filter with low cut off frequency (1200 Hz). The top and bottom portions 200, 202 show the peak-to-peak envelope detected voltage which is displayed in FIG. 4B (bottom). The initial 7 seconds correspond to the baseline; i.e., electrodes in the blood stream. The next 7 seconds correspond to an injection of hyper-osmotic NaCl solution (1.5% NaCl). It can be seen that the voltage is decreased implying increase conductance (since the injected current is constant). Once the NaCl solution is washed out, the baseline is recovered as can be seen in the last portion of the FIGS. 4A and 4B. FIGS. 5A and 5B show similar data corresponding to 0.5% NaCl solutions.

The voltage signals are ideal since the difference between the baseline and the injected solution is apparent and systematic. Furthermore, the pulsation of vessel diameter can be seen in the 0.5% and 1.5% NaCl injections (FIGS. 4 and 5, respectively). This allows determination of the variation of CSA throughout the cardiac cycle as outline above.

The NaCl solution can be injected by hand or by using a mechanical injector to momentarily displace the entire volume of blood or bodily fluid in the vessel segment of interest. The pressure generated by the injection will not only displace the blood in the antegrade direction (in the direction of blood flow) but also in the retrograde direction (momentarily push the blood backwards). In other visceral organs which may be normally collapsed, the NaCl solution will not displace blood as in the vessels but will merely open the organs and create a flow of the fluid. In one approach, after injection of a first solution into the treatment or measurement site, sensors monitor and confirm baseline of conductance prior to injection of a second solution into the treatment site.

The injections described above are preferably repeated at least once to reduce errors associated with the administration of the injections, such as, for example, where the injection does not completely displace the blood or where there is significant mixing with blood. It will be understood that any bifurcation(s) (with branching angle near 90 degrees) near the targeted luminal organ can cause an overestimation of the calculated CSA. Hence, generally the catheter should be slightly retracted or advanced and the measurement repeated. An additional application with multiple detection electrodes or a pull back or push forward during injection will accomplish the same goal. Here, an array of detection electrodes can be used to minimize or eliminate errors that would result from bifurcations or branching in the measurement or treatment site.

In one approach, error due to the eccentric position of the electrode or other imaging device can be reduced by inflation of a balloon on the catheter. The inflation of balloon during measurement will place the electrodes or other imaging device in the center of the vessel away from the wall. In the case of impedance electrodes, the inflation of balloon can be synchronized with the injection of bolus where the balloon inflation would immediately precede the bolus injection. Our results, however, show that the error due to catheter eccentricity is small.

The CSA predicted by Equation[4] corresponds to the area of the vessel or organ external to the catheter (i.e., CSA of vessel minus CSA of catheter). If the conductivity of the NaCl solutions is determined by calibration from Equation [10] with various tubes of known CSA, then the calibration accounts for the dimension of the catheter and the calculated CSA corresponds to that of the total vessel lumen as desired. In one embodiment, the calibration of the CSA measurement system will be performed at 37° C. by applying 100 mmHg in a solid polyphenolenoxide block with holes of known CSA ranging from 7.065 $mm^2$ (3 mm in diameter) to 1017 $mm^2$ (36 in mm). If the conductivity of the solutions is obtained from a conductivity meter independent of the catheter, however, then the CSA of the catheter is generally added to the CSA computed from Equation[4] to give the desired total CSA of the vessel.

The signals are generally non-stationary, nonlinear and stochastic. To deal with non-stationary stochastic functions, one can use a number of methods, such as the Spectrogram, the Wavelet's analysis, the Wigner-Ville distribution, the Evolutionary Spectrum, Modal analysis, or preferably the intrinsic model function (IMF) method. The mean or peak-to-peak values can be systematically determined by the aforementioned signal analysis and used in Equation[4] to compute the CSA.

Figure 6:
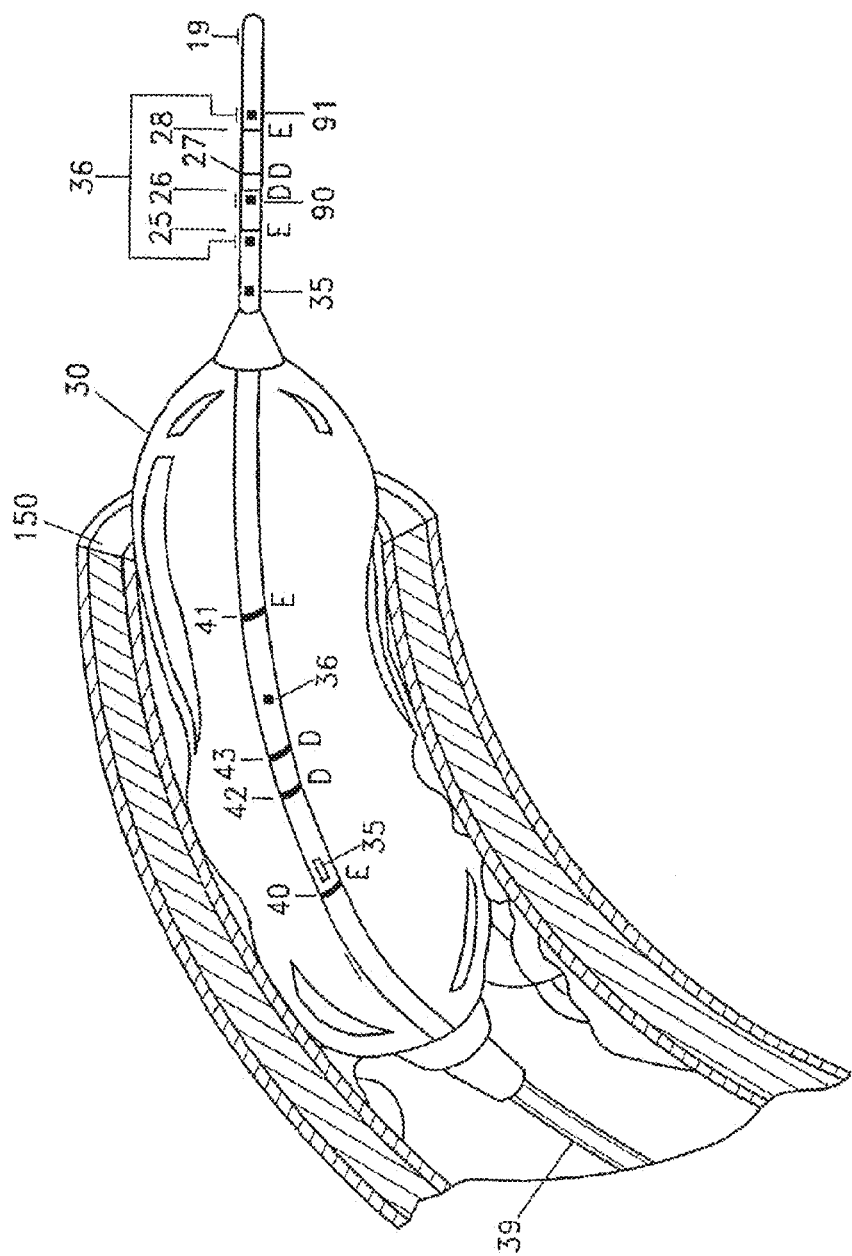
FIG. 6 shows balloon distension of the lumen of the coronary artery, according to an embodiment of the present disclosure.
Figure 7A:
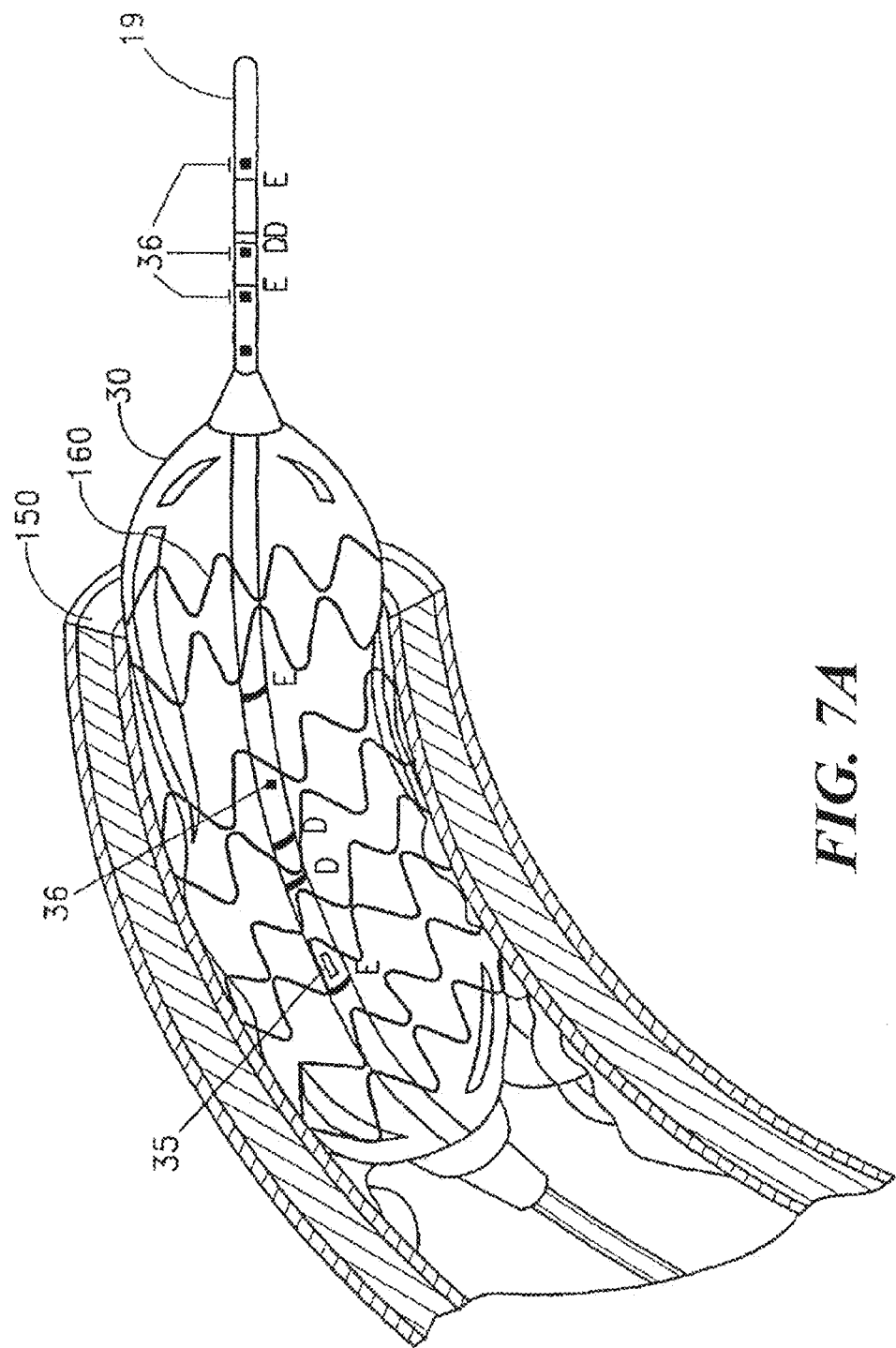
FIG. 7A shows balloon distension of a stent into the lumen of the coronary artery, according to an embodiment of the present disclosure.

Referring to the embodiment shown in FIG. 6, the angioplasty balloon 30 is shown distended within the coronary artery 150 for the treatment of stenosis. As described above with reference to FIG. 1B, a set of excitation electrodes 40, 41 and detection electrodes 42, 43 are located within the angioplasty balloon 30. In another embodiment, shown in FIG. 7A, the angioplasty balloon 30 is used to distend the stent 160 within blood vessel 150.

For valve area determination, it is not generally feasible to displace the entire volume of the heart. Hence, the conductivity of blood is changed by injection of hypertonic NaCl solution into the pulmonary artery which will transiently change the conductivity of blood. If the measured total conductance is plotted versus blood conductivity on a graph, the extrapolated conductance at zero conductivity corresponds to the parallel conductance. In order to ensure that the two inner electrodes are positioned in the plane of the valve annulus (2-3 mm), in one preferred embodiment, the two pressure sensors 36 are advantageously placed immediately proximal and distal to the detection electrodes (1-2 mm above and below, respectively) or several sets of detection electrodes (see, e.g., FIGS. 1D and 1F). The pressure readings will then indicate the position of the detection electrode relative to the desired site of measurement (aortic valve: aortic-ventricular pressure; mitral valve: left ventricular-atrial pressure; tricuspid valve: right atrial-ventricular pressure; pulmonary valve: right ventricular-pulmonary pressure). The parallel conductance at the site of annulus is generally expected to be small since the annulus consists primarily of collagen which has low electrical conductivity. In another application, a pull back or push forward through the heart chamber will show different conductance due to the change in geometry and parallel conductance. This can be established for normal patients which can then be used to diagnose valvular stensosis.

In one approach, for the esophagus or the urethra, the procedures can conveniently be done by swallowing fluids of known conductances into the esophagus and infusion of fluids of known conductances into the urinary bladder followed by voiding the volume. In another approach, fluids can be swallowed or urine voided followed by measurement of the fluid conductances from samples of the fluid. The latter method can be applied to the ureter where a catheter can be advanced up into the ureter and fluids can either be injected from a proximal port on the probe (will also be applicable in the intestines) or urine production can be increased and samples taken distal in the ureter during passage of the bolus or from the urinary bladder.

In one approach, concomitant with measuring the cross-sectional area and or pressure gradient at the treatment or measurement site, a mechanical stimulus is introduced by way of inflating the balloon or by releasing a stent from the catheter, thereby facilitating flow through the stenosed part of the organ. In another approach, concomitant with measuring the cross-sectional area and or pressure gradient at the treatment site, one or more pharmaceutical substances for diagnosis or treatment of stenosis is injected into the treatment site. For example, in one approach, the injected substance can be smooth muscle agonist or antagonist. In yet another approach, concomitant with measuring the cross-sectional area and or pressure gradient at the treatment site, an inflating fluid is released into the treatment site for release of any stenosis or materials causing stenosis in the organ or treatment site.

Again, it will be noted that the methods, systems, and catheters described herein can be applied to any body lumen or treatment site. For example, the methods, systems, and catheters described herein can be applied to any one of the following exemplary bodily hollow systems: the cardiovascular system including the heart; the digestive system; the respiratory system; the reproductive system; and the urogential tract.

Finite Element Analysis:

In one preferred approach, finite element analysis (FEA) is used to verify the validity of Equations [4] and [5]. There are two major considerations for the model definition: geometry and electrical properties. The general Equation governing the electric scalar potential distribution, $V$, is given by Poisson's Equation as:

$$\nabla \cdot (CVV) = -I \qquad [13]$$

where $C$, $I$ and $\nabla$ are the conductivity, the driving current density and the del operator, respectively. Femlab or any standard finite element packages can be used to compute the nodal voltages using Equation[13]. Once $V$ has been determined, the electric field can be obtained from as $E = -\nabla V$.

The FEA allows the determination of the nature of the field and its alteration in response to different electrode distances, distances between driving electrodes, wall thicknesses and wall conductivities. The percentage of total current in the lumen of the vessel (% I) can be used as an index of both leakage and field homogeneity. Hence, the various geometric and electrical material properties can be varied to obtain the optimum design; i.e., minimize the non-homogeneity of the field. Furthermore, we simulated the experimental procedure by injection of the two solutions of NaCl to verify the accuracy of Equation[4]. Finally, we assessed the effect of presence of electrodes and catheter in the lumen of vessel. The error terms representing the changes in measured conductance due to the attraction of the field to the electrodes and the repulsion of the field from the resistive catheter body were quantified.

We solved the Poisson's Equation for the potential field which takes into account the magnitude of the applied current, the location of the current driving and detection electrodes, and the conductivities and geometrical shapes in the model including the vessel wall and surrounding tissue. This analysis suggest that the following conditions are optimal for the cylindrical model: (1) the placement of detection electrodes equidistant from the excitation electrodes; (2) the distance between the current driving electrodes should be much greater than the distance between the voltage sensing electrodes; and (3) the distance between the detection and excitation electrodes is comparable to the vessel diameter or the diameter of the vessel is small relative to the distance between the driving electrodes. If these conditions are satisfied, the equipotential contours more closely resemble straight lines perpendicular to the axis of the catheter and the voltage drop measured at the wall will be nearly identical to that at the center. Since the curvature of the equipotential contours is inversely related to the homogeneity of the electric field, it is possible to optimize the design to minimize the curvature of the field lines. Consequently, in one preferred approach, one or more of conditions (1)-(3) described above are met to increase the accuracy of the cylindrical model.

Figure 7B:
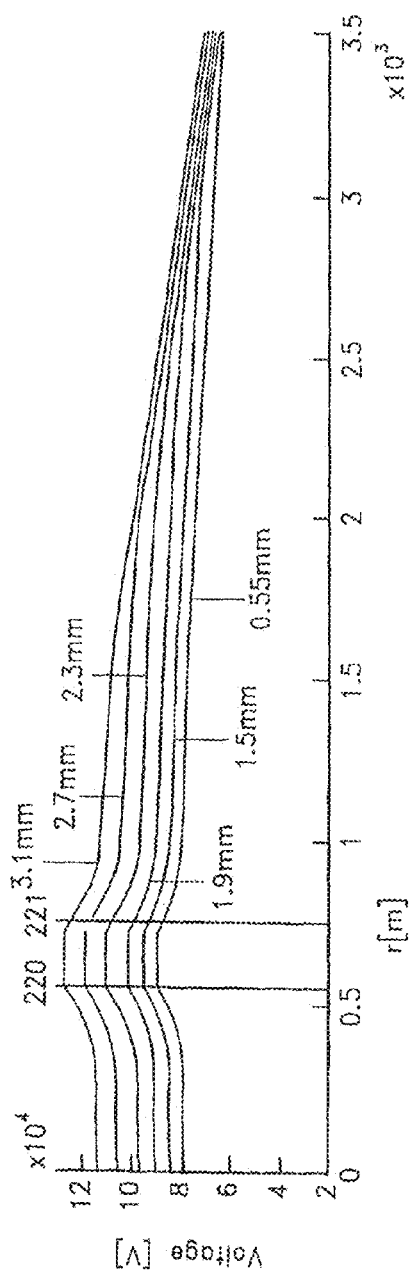
FIG. 7B shows the voltage recorded by a conductance catheter with a radius of 0.55 mm for various size vessels (vessel radii of 3.1, 2.7, 2.3, 1.9, 1.5 and 0.55 mm for the six curves, respectively) when a 0.5% NaCl bolus is injected into the treatment site, according to an embodiment of the present disclosure.
Figure 7C:
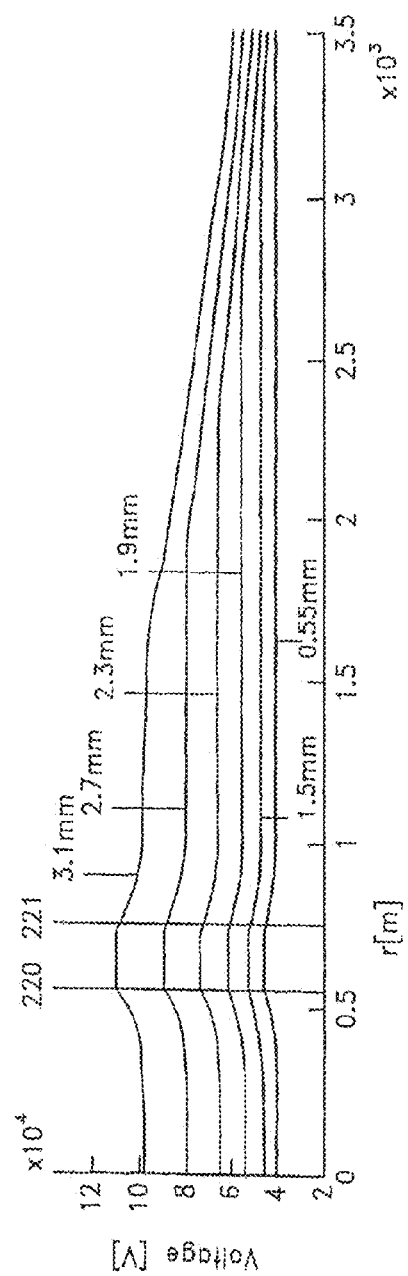
FIG. 7C shows the voltage recorded by a conductance catheter with a radius of 0.55 mm for various size vessels (vessel radii of 3.1, 2.7, 2.3, 1.9, 1.5 and 0.55 mm for the six curves, respectively) when a 1.5% NaCl bolus is injected into the treatment site, according to an embodiment of the present disclosure.

Theoretically, it is impossible to ensure a completely homogeneous field given the current leakage through the vessel wall into the surrounding tissue. We found that the iso-potential line is not constant as we move out radially along the vessel as stipulated by the cylindrical model. In one embodiment, we consider a catheter with a radius of 0.55 mm whose detected voltage is shown in FIGS. 7B and 7C for two different NaCl solutions (0.5% and 1.5%, respectively). The origin corresponds to the center of the catheter. The first vertical line 220 represents the inner part of the electrode which is wrapped around the catheter and the second vertical line 221 is the outer part of the electrode in contact with the solution (diameter of electrode is approximately 0.25 mm). The six different curves, top to bottom, correspond to six different vessels with radii of 3.1, 2.7, 2.3, 1.9, 1.5 and 0.55 mm, respectively. It can be seen that a "hill" occurs at the detection electrode 220, 221 followed by a fairly uniform plateau in the vessel lumen followed by an exponential decay into the surrounding tissue. Since the potential difference is measured at the detection electrode 220, 221, our simulation generates the "hill" whose value corresponds to the equivalent potential in the vessel as used in Equation[4]. Hence, for each catheter size, we varied the dimension of the vessel such that Equation[4] is exactly satisfied. Consequently, we obtained the optimum catheter size for a given vessel diameter such that the distributive model satisfies the lumped Equations (Equation[4] and [5]).

In this way, we can generate a relationship between vessel diameter and catheter diameter such that the error in the CSA measurement is less than 5%. In one embodiment, different diameter catheters are prepackaged and labeled for optimal use in certain size vessel. For example, for vessel dimension in the range of 4-5 mm, 5-7 mm or 7-10 mm, our analysis shows that the optimum diameter catheters will be in the range of 0.91.4, 1.4-2 or 2-4.6 mm, respectively. The clinician can select the appropriate diameter catheter based on the estimated vessel diameter of interest. This decision will be made prior to the procedure and will serve to minimize the error in the determination of lumen CSA.

Percutaneous Valve and Valve Annulus Sizing

In addition to the foregoing, the disclosure of the present application discloses various devices, systems, and methods for sizing a percutaneous valve and/or a valve annulus and placing replacement valves within a luminal organ using a balloon.

Figure 8A:
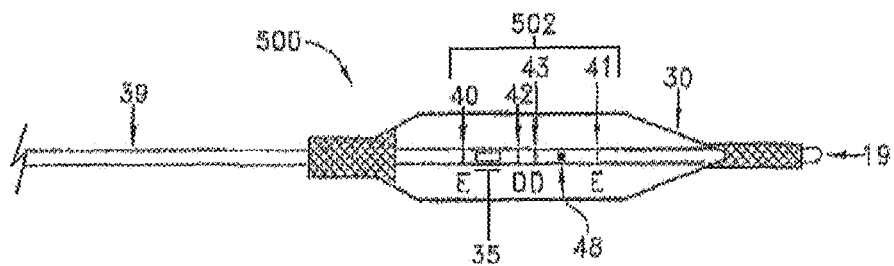
FIGS. 8A, 8B, and 8C show various embodiments of devices for sizing a percutaneous valve and/or a valve annulus, according to embodiments of the present disclosure.

An exemplary embodiment of a device for sizing a valve annulus 500 of the present disclosure is shown in FIG. 8A. As shown in FIG. 8A, an exemplary device 500 comprises a catheter 39 and a balloon 30 positioned thereon at or near the tip 19 (distal end) of catheter 39 so that any gas and/or fluid injected through catheter 20 into balloon 30 by way of a suction/infusion port 35 will not leak into a patient's body when such a device 500 is positioned therein.

Figure 8B:
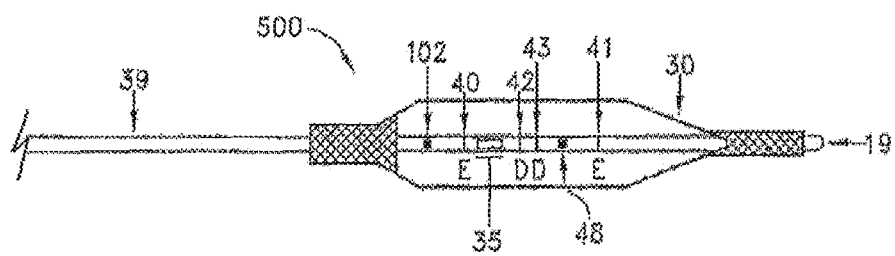

As shown in FIGS. 8A and 8B, device 500 comprises a detector 502, wherein detector 502, in at least one embodiment, comprises a tetrapolar arrangement of two excitation electrodes 40, 41 and two detection electrodes 42, 43 located inside balloon 30 for accurate determination of the balloon 30 cross-sectional area during sizing of a valve annulus. Such a tetrapolar arrangement (excitation, detection, detection, and excitation, in that order) as shown in FIG. 8A would allow sizing of the space within balloon 30, including the determination of balloon 30 cross-sectional area. As shown in FIG. 8A, device 500 comprises a catheter 39 (an exemplary elongated body), wherein balloon 30 is positioned thereon at or near the tip 19 (distal end) of catheter 39. In addition, an exemplary embodiment of a device 500, as shown in FIG. 8A, comprises a pressure transducer 48 capable of measuring the pressure of a gas and/or a liquid present within balloon 30. Device 500 also has a suction/infusion port 35 defined within catheter 39 inside balloon 30, whereby suction/infusion port 35 permits the injection of a gas and/or a fluid from a lumen of catheter 39 into balloon 30, and further permits the removal of a gas and/or a fluid from balloon 30 back into catheter 39.

Figure 8C:
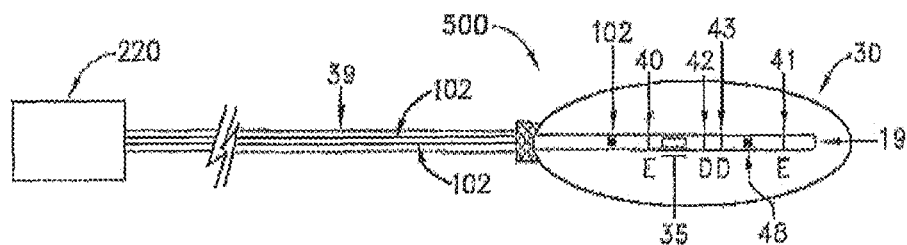

FIG. 8C, as referenced above, shows another exemplary embodiment of a device 500 of the present disclosure. FIG. 8C comprises several of the same components shown in the embodiments of a device 500 of the present disclosure shown in FIGS. 8A and 8B, but as shown in FIG. 8C, balloon 30 does not connect to catheter 39 at both relative ends of balloon 30. Instead, balloon 30 is coupled to catheter 39 proximal to electrodes 40, 41, 42, and 43, and is not coupled to catheter 39 distal to said electrodes. In addition, the exemplary embodiment of device 500 shown in FIG. 8C comprises a data acquisition and processing system 220 coupled thereto. The exemplary embodiments of devices 500 shown in FIGS. 8A and 8C are not intended to be the sole embodiments of said devices 500, as various devices 500 of the present disclosure may comprise additional components as shown in various other figures and described herein.

Figure 8D:
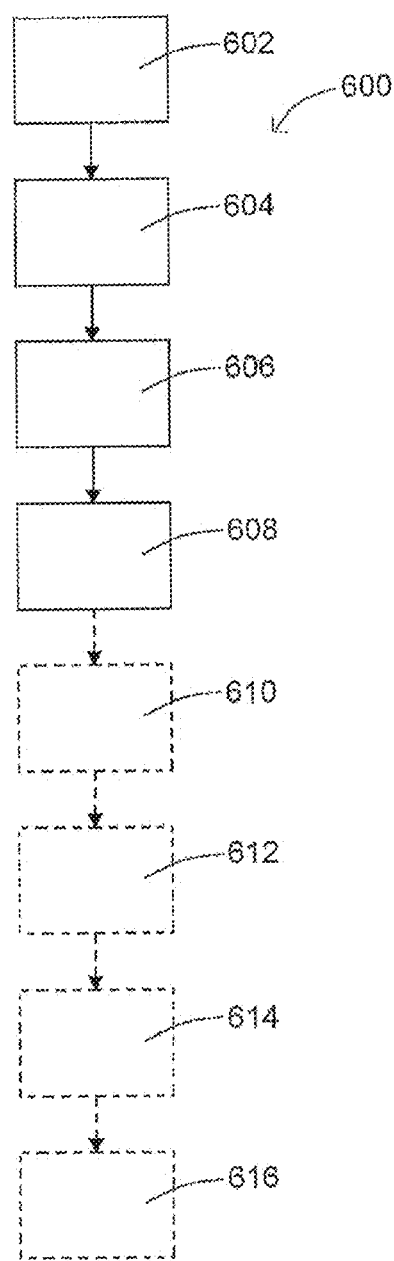
FIG. 8D shows steps of an exemplary method to size a percutaneous valve and/or a valve annulus, according to the present disclosure.

Various exemplary embodiments of devices 500 of the present disclosure may be used to size a valve annulus as follows. In at least one embodiment of a method to size a valve annulus of the present disclosure, method 600, as shown in FIG. 8D, comprises the steps of introducing at least part of a sizing device into a luminal organ at a valve annulus (an exemplary introduction step 602), wherein the sizing device 500 comprises a detector 502 and a pressure transducer 48 within a balloon 30 at or near a distal end 19 of sizing device 500. Method 600 then comprises the steps of inflating balloon 30 until a threshold pressure is detected by pressure transducer 48 within balloon 30 (an exemplary inflation step 604), and obtaining a first valve annulus measurement using detector 504 (an exemplary measurement step 606). In at least one embodiment, balloon 30 has a larger diameter than the valve annulus to be sized, so that when balloon 30 is initially inflated (inflation step 604), the diameter of balloon 30 will increase but the pressure of the balloon 30 will remain small because of excess balloon 30. Once the diameter of balloon 30 reaches the border of the annulus, the measured balloon pressure will begin to rise. In an exemplary inflation step 604, inflation step 604 comprises the step of introducing a fluid into a lumen of device 500, through a suction/infusion port 35, and into balloon 30. At the point of apposition (significant pressure rise, also referred to herein as a "threshold pressure"), the size of balloon 30 will correspond to the size of the annulus and hence the desired measurement. When a threshold pressure is reached within balloon 30, measurement step 606 may be performed to obtain an optimal first valve annulus measurement.

An exemplary measurement step 606 of method 600, in at least one embodiment, comprises measuring a balloon 30 cross-sectional area using detector 502. In an exemplary embodiment, measurement step 606 is performed when a threshold pressure is present within balloon 30. In at least one embodiment, the balloon 30 cross-sectional area is determined from a conductance measurement of a fluid present within balloon 30 obtained by detector 502, a known conductivity of the fluid, and a known distance between detection electrodes 41, 42.

Figure 9A:
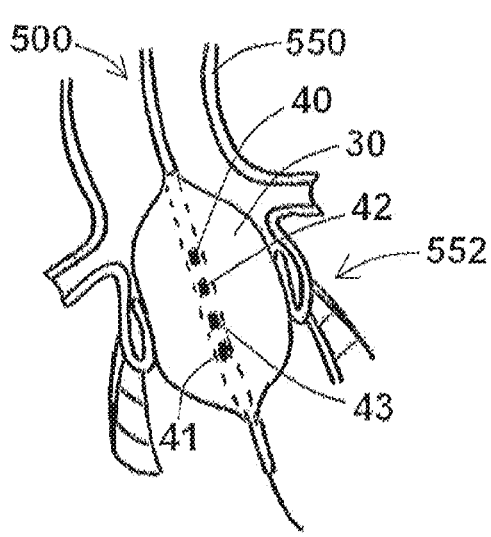
FIGS. 9A, 9B, and 9C show an exemplary embodiment of a sizing device of the present disclosure obtaining sizing data within a luminal organ (FIG. 9A), deflated but having a stent valve positioned around the device (FIG. 9B), and inflated to place the stent valve (FIG. 9C), according to embodiments of the present disclosure.

FIG. 9A shows an exemplary embodiment of a sizing device 500 positioned within a luminal organ 550 at a valve annulus 552. Device 500 is shown in FIG. 9A with an inflated balloon 30, with electrodes 40, 41, 42, 43 defined within the figure. At the time a threshold pressure within balloon 30 is identified by pressure transducer 48, electrodes 40, 41, 42, 43 (a detector 502 as referenced herein) may operate to obtain a first valve annulus measurement, such as a valve annulus cross-sectional area, corresponding to the cross-sectional area of balloon 30. Such a measurement (measurement step 606) is a more precise valve annulus measurement that can be obtained either visually (under fluoroscopy) or using pressure alone.

After measurement step 606 is performed, and in at least one embodiment of a method 600 of the present disclosure, method 600 further comprises the steps of withdrawing sizing device 500 from luminal organ 550 (an exemplary device withdrawal step 608). In an exemplary device withdrawal step 608, device withdrawal step 608 comprises the step of removing fluid from balloon 30, through suction/infusion port 35, and into the lumen of device 500, to deflate balloon 30. In at least one embodiment of method 600 comprises the optional steps of positioning a stent valve 560 (as shown in FIGS. 9B-9D) upon balloon 30 (an exemplary stent valve positioning step 610), reintroducing at least part of device 500 back into luminal organ 550 at valve annulus 552 (an exemplary reintroduction step 612), and reinflating balloon 30 to a desired inflation to place stent valve 560 within valve annulus 552 (an exemplary stent valve placement step 614).

Figure 9B:
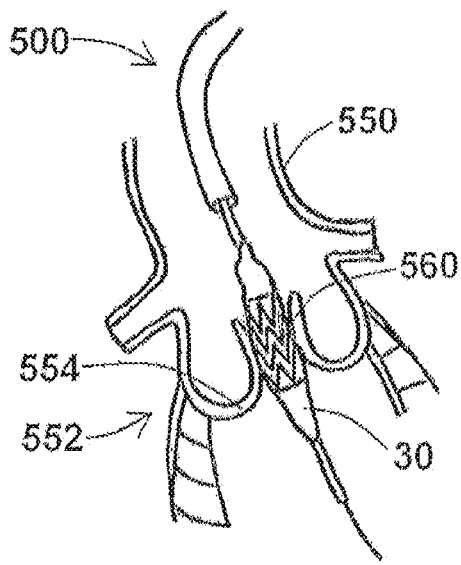
Figure 9C:
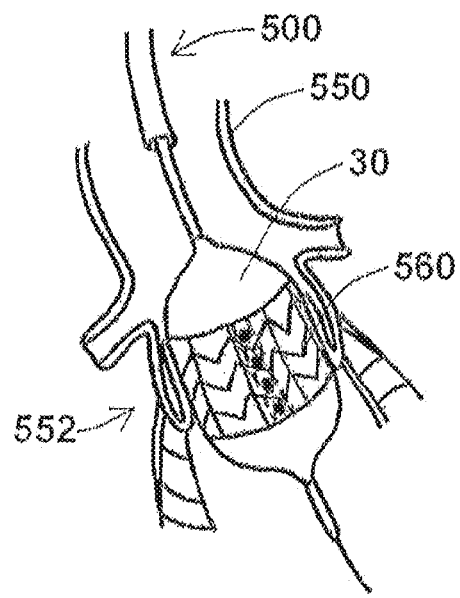
Figure 9D:
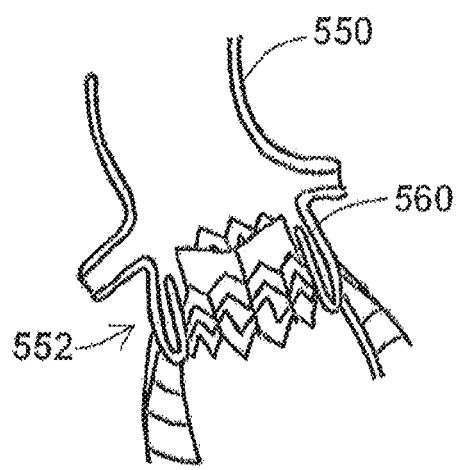
FIG. 9D shows a stent valve positioned within a luminal organ, according to an embodiment of the present disclosure.

At least some of the aforementioned steps of method 600 are also shown in FIGS. 9B-9D. As shown in FIG. 9B, and once the valve annulus has been sized using method 600 of the present disclosure, an appropriate size stent can then be placed within luminal organ 550. Detector 502, after a stent valve 560 has been positioned upon balloon 30, can then size balloon 30 carrying stent valve 560. FIG. 9B shows at least part of device 500 having stent valve 560 positioned upon a relatively or completely deflated balloon 30, and FIG. 9C shows the same device 500 having an inflated balloon 30 to place stent valve 560 within luminal organ 550. Balloon 30, as shown in FIG. 9C, is inflated until the desired size of stent valve 560 is reached to ensure the desired apposition. Since the wall thickness of balloon 30 is known, the size of balloon 30, when inflated, will reflect the size of stent valve 560. Device 500 can then be removed from luminal organ 550 (an exemplary device rewithdrawal step 616), wherein stent valve 560 remains positioned within luminal organ 550 at valve annulus 552.

FIG. 9B is also indicative of sizing a percutaneous valve 554 itself, whereby the percutaneous valve flaps are visible in FIG. 9B. Such sizing may be performed using an exemplary method 600 of the present disclosure, whereby an exemplary inflation step 604 comprises inflating balloon 30 at the site of percutaneous valve 554 until a threshold pressure is met, and whereby an exemplary measurement step 606 comprises obtaining a percutaneous valve opening measurement using detector 504.

Figure 10:
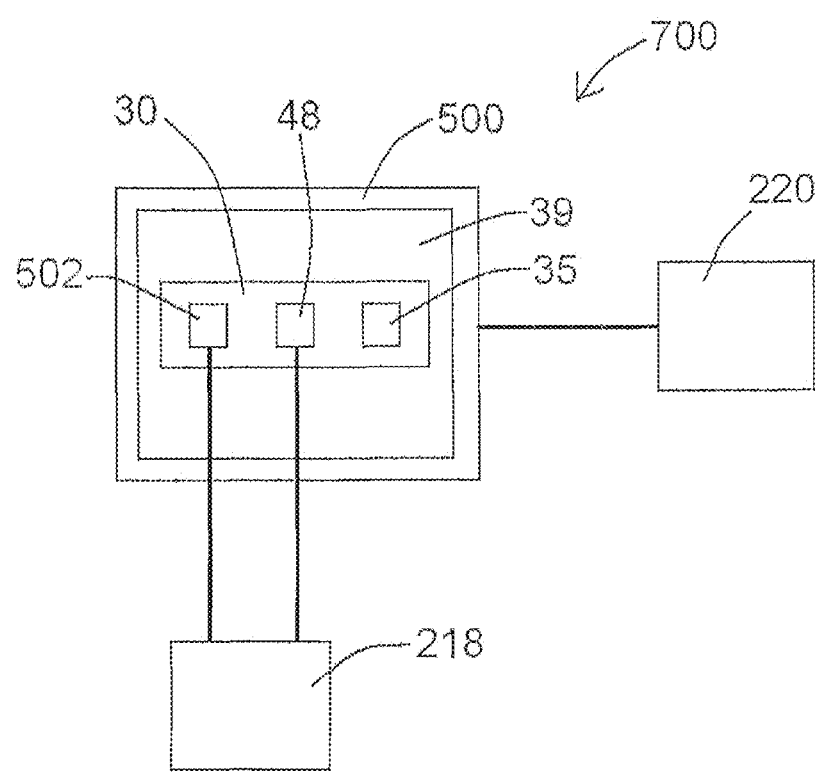
FIG. 10 shows a block diagram of an exemplary system for sizing a percutaneous valve and/or a valve annulus, according to an embodiment of the present disclosure.

An exemplary system for sizing a percutaneous valve and/or a valve annulus of the present disclosure is shown in the block diagram shown in FIG. 10. As shown in FIG. 10, system 700 comprises a device 500, a data acquisition and processing system 220 coupled thereto, and a current source 218 coupled to a detector 502 and a pressure transducer 48 of device 500. Device 500, as shown in FIG. 10, may comprise a catheter 39 (an exemplary elongated body) having a balloon 30 coupled thereto, wherein detector 502 and pressure transducer 48 are positioned along catheter 39 within balloon 30. A suction/infusion port 35 may also be defined within catheter 39, as referenced herein, to facilitate the movement of a fluid in and out of balloon 30 from catheter 39.

As referenced herein, a modified version of Ohm's law may be used, namely:

$$CSA = (G/L)/\alpha \quad [14]$$

wherein CSA is the cross-sectional area of balloon 30, G is the electrical conductance given by a ratio of current and voltage drop (I/V, wherein I represents injected current and V is the measured voltage drop along detection electrodes 41, 42), L is a constant for the length of spacing between detection electrodes 41, 42 of sizing device 500, and $\alpha$ is the electrical conductivity of the fluid within balloon 30. Equation[14] can then be used to provide CSA in real time given the conductivity of fluid used to inflate the balloon (such as, for example, half normal saline (0.9% NaCl)) and half contrast (iodine, etc.), the measure conductance (G) and the known distance L.

Figure 11:
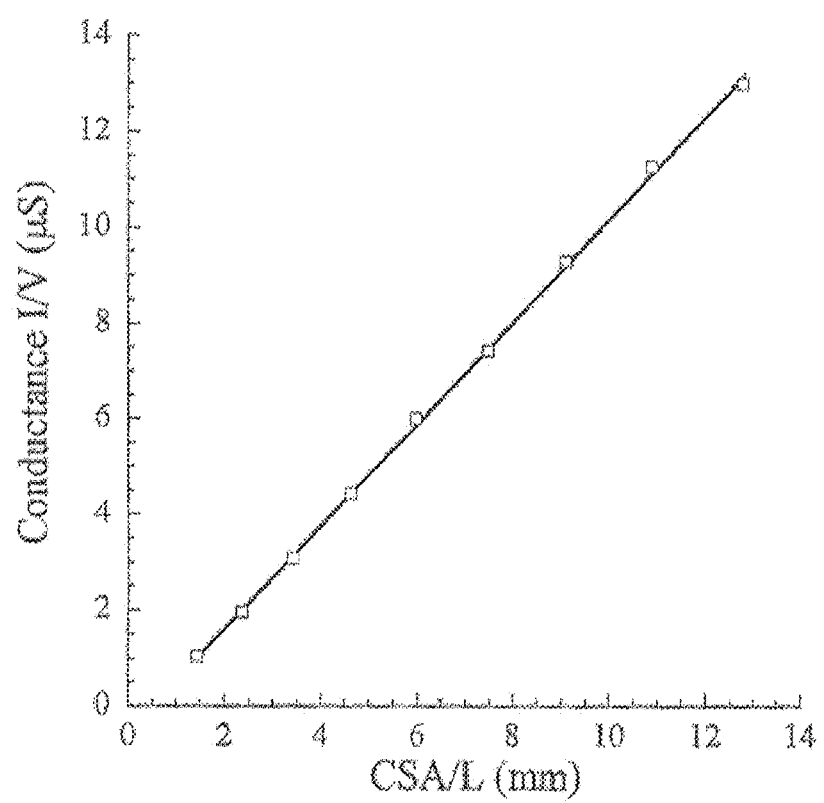
FIG. 11 shows calibration data of an exemplary sizing device using phantoms having known cross-sectional areas, according to an embodiment of the present disclosure.

A typical calibration curve of an impedance balloon 30 is shown in FIG. 11. As shown in FIG. 11, the slope of the line provides the conductivity ($\alpha$) of fluid within balloon. The solid line shown in FIG. 11 has a linear fit of the form $y=1.00664 \times x - 0.4863$, wherein $R^2=0.99$. Calibration, in at least this example, was performed using various phantoms having known CSAs.

Such embodiments of devices 500 of the present disclosure have several advantages. First, electrodes 40, 41, 42, and 43 are positioned along catheter 39 within balloon 30, so minimal risk to damage of said electrodes arises. Second, and since balloon 30 insulates the electric field generated by excitation electrodes 40, 41, there is no parallel conductance and hence no need for two injections to obtain a desired measurement. In addition, said devices 500 incorporate the ability to size a valve and/or a valve annulus and can also deliver a stent valve 560 as referenced herein. Using Equation[14] for example, real-time measurements of CSA can be obtained as desired, with no additional procedures required by a physician. The sizing results are quite accurate (as shown in FIG. 11), providing additional confidence of the sizing measurements without the need for echocardiograms, MRIs, or other expensive imaging mechanisms.

The present disclosure includes disclosure of additional devices useful to obtain sizing measurements within a luminal organ/body. For example, and as shown in FIGS. 12A-12D, side view (FIGS. 12A and 12C) and front views (FIGS. 12B and 12D) of an adjustable device 800 of the present disclosure are shown in two configurations. Proximal ends 802 are displayed to the left and distal ends 804 are displayed to the right in FIGS. 12A and 12C.

Figure 12B:
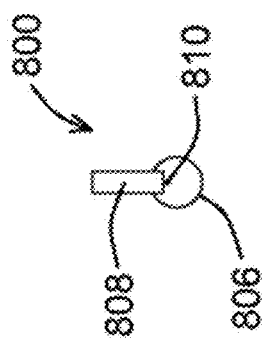
FIG. 12B shows a front end view of at least part of a sizing device, according to an exemplary embodiment of the present disclosure.
Figure 12D:
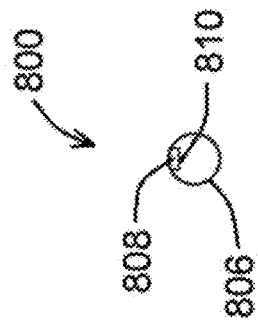
FIGS. 12D, 13, and 14 show front end views of at least part of sizing devices, according to exemplary embodiments of the present disclosure.
Figure 12A:
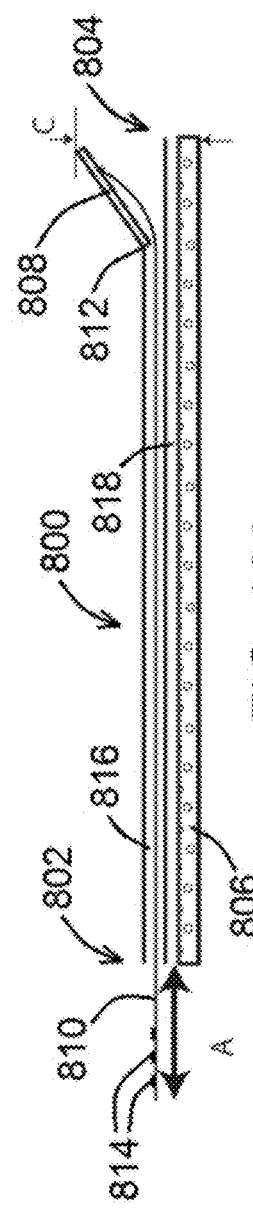
FIG. 12A shows a side view of at least part of a sizing device, according to an exemplary embodiment of the present disclosure.
Figure 12C:
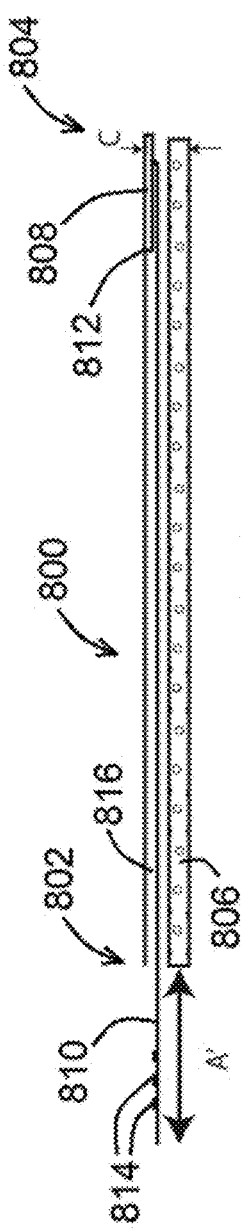
FIG. 12C shows a side view of at least part of a sizing device, according to an exemplary embodiment of the present disclosure.

As shown in FIGS. 12A and 12C, device 800 comprises a body 806 (which may also be referred to as a catheter herein) having a sizing finger 808 incorporated therein or coupled thereto. A control wire 810 is coupled to sizing finger 808 so that advancement of control wire 810 in the direction of proximal end 802 to distal end 804 causes sizing finger 808 to open relative to other portions of body 806, and so that retraction of control wire 810 in the direction of distal end 804 to proximal end 802 causes sizing finger 808 to close relative to other portions of body 806. Sizing finger 808 may pivot relative to hinge 812, as shown in FIGS. 12A and 12C.

Sizing finger 808 may be deflected away from body 806, as shown in FIGS. 12A and 12B, or retracted into and/or toward body 806, as shown in FIGS. 12C and 12D, via control wire 810 as referenced above. At or near proximal end 802, an operator may pull control wire 810 away from body 806 to retract finger 808, and said operator may push control wire 810 towards body 806 to deflect finger 808, as referenced above. As shown in FIGS. 12A and 12C, dimension A is less than dimension A', corresponding to displacement of finger 808. In various embodiments, control wire 810 in the proximal area is marked with indicia 814 reflective of and calibrated to deflection of finger 808. In at least one embodiment, finger 808 is retracted into body 806 prior to insertion within a body vessel/luminal organ 550.

Catheter body 806, as shown in FIGS. 12A and 12C, contains a lumen 816 for control wire 810. Catheter body 806 may further contain/define a pressure lumen 818 to measure distal end pressure. Lumen 816 and pressure lumen 818, as shown in FIG. 12A, may extend from proximal end 802 to distal end 804 of device 100.

In use, catheter body 806 is advanced into a target vessel (luminal organ 550), and finger 808 is deflected away from catheter body 806 until the operator senses resistance owing to engagement of two internal sides of the target vessel 550. The operator may then note the indicia 814 on control wire 810 corresponding to a first measurement. Calibration of the catheter assembly (device 800) prior to insertion in the body reveals the corresponding deflection of finger 808 and the diameter of the target vessel 550.

Figure 13:
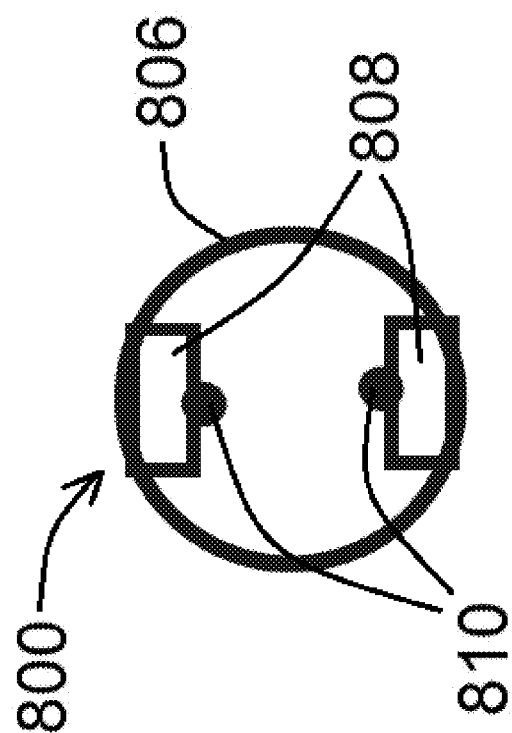

FIG. 13 illustrates an end view of an exemplary device 800 of the present disclosure corresponding to end views of catheter body 806. The catheter body 806 shown in FIG. 13 includes two deflectable fingers 808, diametrically opposed on a catheter body 806. The two deflectable fingers 808 may be deflected independently with independent control wires 810 or may be linked and synchronized for simultaneous and essentially equal deflection.

Figure 14:
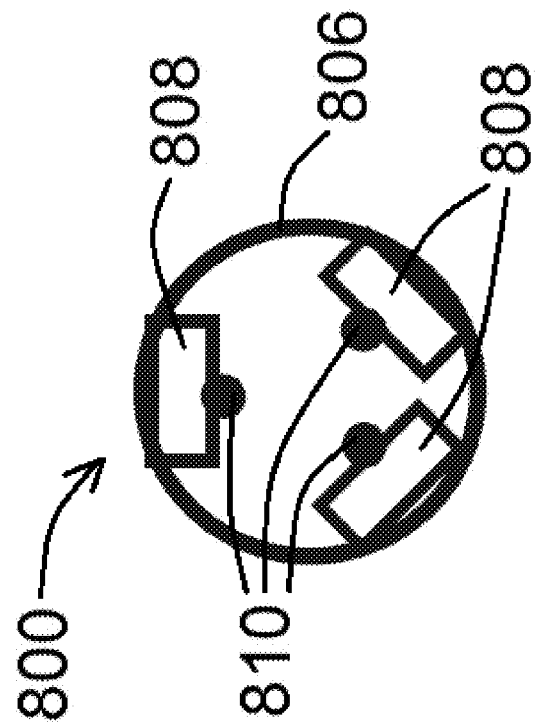

FIG. 14 illustrates an end view of an exemplary device 800 of the present disclosure corresponding to end views of catheter body 806. The catheter shown in FIG. 14 includes three deflectable fingers 808, distributed around a periphery of a catheter body 806. The three deflectable fingers 808 may be deflected independently with independent control wires 814 or may be linked and synchronized for simultaneous and essentially equal deflection. Control wire 810 shown in FIGS. 12A and 12C and control wires 810 shown in FIGS. 13 and 14 may be directly observable by the operator or may be contained within a mechanism (not shown) to facilitate operation and measurement.

FIGS. 15A-15D show another exemplary device 800 embodiment of the present disclosure in two configurations. As shown therein, catheter body 806 includes inner shaft 900, two hinges 812, and two flexible fingers 808. Inner shaft 900 and control wire 806, as referenced herein, may be referred to generally as movable devices. Side views of device 800 are shown in FIGS. 15A and 15C, and end views are shown in FIGS. 15B and 15D. Sliding shaft 900 within catheter body 806 causes flexible fingers 808 to deflect away from catheter body 806, as shown in FIGS. 15A and 15B, or retract into catheter body 806, as shown in FIGS. 15C and 15D. A proximal area near an operator is shown to the left, and a distal area to be inserted into a body is shown to the right. The proximal area of inner shaft 900 is optionally marked with indicia 814 corresponding to deflection of flexible fingers 808 and measurements D, D'. As shaft 900 is pushed into catheter body 806, flexible fingers 808 retract into catheter body 806 and become at the extent of movement, aligned and essentially a continuation of catheter body 806 as shown in FIGS. 15C and 15D. Flexible fingers 808 are retracted into catheter body 806 for insertion into a target vessel 550, for example. Shaft 900 includes a lumen 902 defined therethrough for the proximal measurement of pressure at the distal end 904 of shaft 900 (at the distal end 804 of device 800).

When located at least partially within a target vessel 550, the operator retracts shaft 900 while holding catheter body 806, deflecting flexible fingers 808 until resistance is felt/detected. The operator may then note the indicia 814 revealed on shaft 900 providing an indication of deflection D of flexible fingers 808. The use of a lumen 902 within device 800 allows the use of pressures to determine location. For example, identification of the right atrium and right ventricle may easily be distinguished, as right ventricular pressure is considerably higher than right atrial pressure. Tricuspid valve passage of the catheter assembly (device 800) is marked with a transition in pressure. Flexible fingers 808 may be straight, as illustrated in FIGS. 15A and 15B, curved, or of another shape.

As referenced in connection with the device 800 shown in FIGS. 12A-15D, for example, valve annulus or valve aperture sizing may be accomplished by placing distal end 804 of the a catheter assembly (device 800) distal to the annulus, deflecting flexible finger(s) 800 to an operator specified dimension and pulling on the catheter assembly (device 800) to determine whether the assembly passes the annulus without resistance. If no resistance is encountered, the annulus is presumed to be larger than the deflected finger 808 dimension. The catheter assembly (device 800) is repositioned distal to the annulus, the fingers 808 further deflected and the procedure repeated until the catheter assembly (device 800) passes through the annulus with slight resistance.

Another embodiment of the catheter assembly of FIGS. 15A-15D includes additional or fewer flexible fingers 808. The number of flexible fingers 808 may be one or more. The catheter assemblies (devices 800) referenced above may be flexible to allow positioning in tortuous anatomical structures, may have tubular components to transfer torque to twist the devices 800 and sufficient tensile strength to facilitate deflection and operator assessment of resistance when gauging vessel lumen size.

Devices 800, as referenced herein, may be utilized to size a vessel lumen or an orifice. Devices 800 may be retracted (i.e., fingers 808 retracted into a general axis defined by a length of device 800) to allow insertion into the body and positioning of the assembly in a target volume. Device 800 may be positioned by fluoroscopy/x-ray and/or fluid pressure measured at the distal tip 804/902 of the device 800 and/or an electrogram (measured from one or more distal electrode(s) not shown in FIGS. 12A-15D, but shown and described herein in connection with other devices (such as, for example, catheters 20, 21, 22, 39, wire 19, device 500, etc.) referenced herein. For example, to position at a tricuspid valve, the electrogram in the right atrium has large atrial and small ventricular constituents. Passing the tricuspid valve into the right ventricle, the atrial electrogram decreases substantially and the ventricular electrogram has a corresponding but larger increase. Similarly, distal fluid pressure is small in the right atrium with very little phasic change. Passing the catheter assembly (device 800) through the tricuspid valve into the right ventricle, distal fluid pressure becomes pronounced with dramatic phasic pressure waves associated with right ventricular contraction. Once positioned in a vessel of interest, finger(s) 808 of device 800 is/are expanded by use of control wire(s) 810 or inner shaft 900. The amount of expansion (shown as C in FIGS. 12A and 12C and shown as D in FIGS. 15A and 15C) may be determined by use of calibration indicia 814 on control wire 810 or inner shaft 900, depending on the device 800 embodiment used. The amount of expansion may also be determined by the use of one or more piezoelectric elements 950 (which may comprise or also refer to one or more piezo or piezoelectric crystals, elements, sensors, disks, and the like) placed on the tip 952 of finger 808 (as shown in FIG. 15B) or at one of hinge points 820 as shown in FIG. 15A. Transmission of a signal generated in one crystal 950 allows reception of the signal at a corresponding crystal 950 at the distal tip 804 of catheter body 806 or at opposing hinge points 820. Measurement of the transmission time between two crystals 950 may be translated into distance given knowledge of transmission time through a fluid in the target volume.

Figure 16:
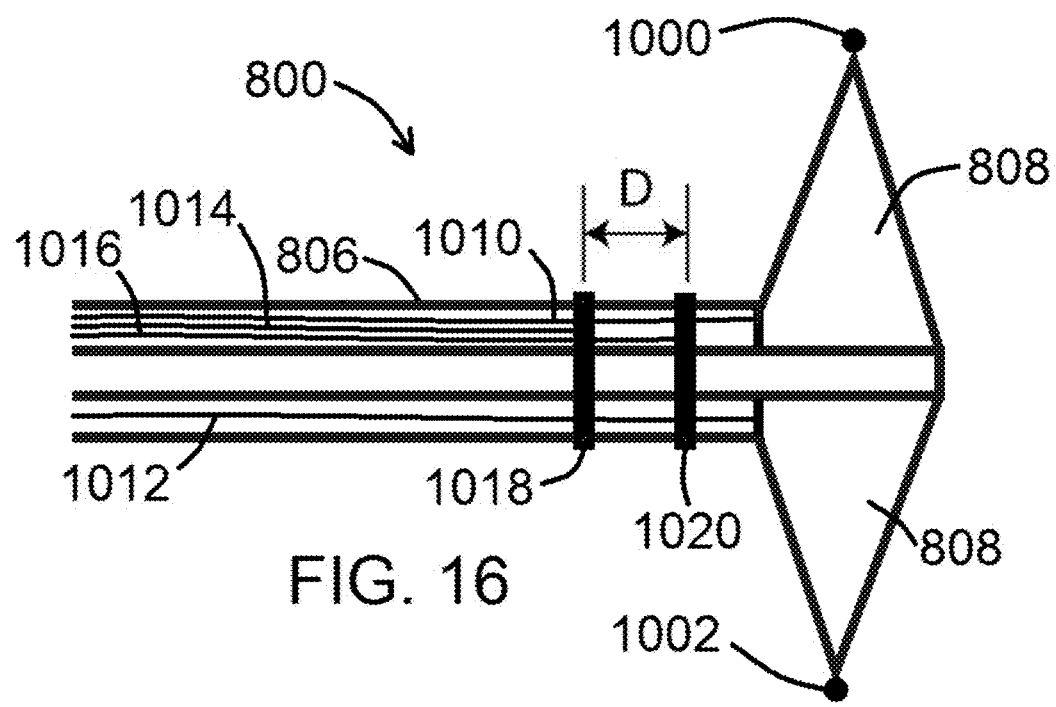
FIGS. 16, 17, and 18 show side views of at least part of sizing devices, according to exemplary embodiments of the present disclosure.

The amount of expansion may also be determined by three dimensional impedance measurement systems, including the various impedance devices and systems referenced herein. In such an embodiment, a pair of electrodes 1000, 1002 (which may be any number/type of electrodes referenced herein) is placed at the tip of finger 808 (as shown in the exemplary distal portion of a device 800 shown in FIG. 16), the distal tip 804 of catheter body 806, or at hinge points 820. The distance between pairs of electrodes 1000, 1002 serves to provide a reference for distance measurements. Each electrode 1000, 1002 is connected to the measurement system (an exemplary data acquisition system 100 of the present disclosure) via one or more wires 1010, 1012 running to the proximal end 802 of the catheter body 806. In at least one embodiment, electrode 1000 connects to data acquisition system 100 (not shown in FIG. 16, but shown in FIG. 3 connected to catheter 20, which is an exemplary device of the present disclosure) using wire 1010, and electrode 1002 connects to data acquisition system 1000 using wire 1012. In at least one embodiment of a device 800 of the present disclosure, and as shown in FIG. 16, device 800 comprises other/additional electrodes, identified as electrodes 1018 and 1020, which are affixed/coupled to body 806 and connect to data acquisition system 100 via additional wires 1014, 1016. As shown in FIG. 16, electrodes 1018 and 1020 are separated by a distance D, and the difference in voltage measured between electrodes 1018, 1020, referred to herein as $|V_{1018-1020}|$, is a function of distance D. Similarly, the difference in voltage measured between electrodes 1000 and 1002, referred to herein as $|V_{1000-1002}|$, is a function between the distance between electrodes 1000 and 1002. In such an overall embodiment, the distance between electrodes is $D \times (|V_{1000-1002}|)/(|V_{1018-1020}|)$. For such embodiments, voltages are measured in orthogonal axes and are treated as vectors in a three-dimensional space.

In various embodiments, and as referenced herein, each electrode used is connected to data acquisition system 100 using a separate wire. The voltage of each electrode, as generally referenced above and referenced in further detail herein, is measured with respect to a reference electrode (such as electrodes 1000, 1002 measuring voltage in view of one another and/or electrodes 1018, 1020 measuring voltage in view of one another). In one exemplary embodiment, for example, one electrode serves as a reference electrode, and it can be used to measure voltage from all electrodes. Should a distance between two electrodes not be known, a distance reference may be used to calibrate the measurement, such as a device of the present disclosure or another device having at least two electrodes thereon with known spacing therebetween. For example, the distance between two electrodes of unknown spacing may be determined by measuring the voltage at each electrode and comparing the measured voltage to the voltage difference between the aforementioned distance reference electrodes.

Figure 17:
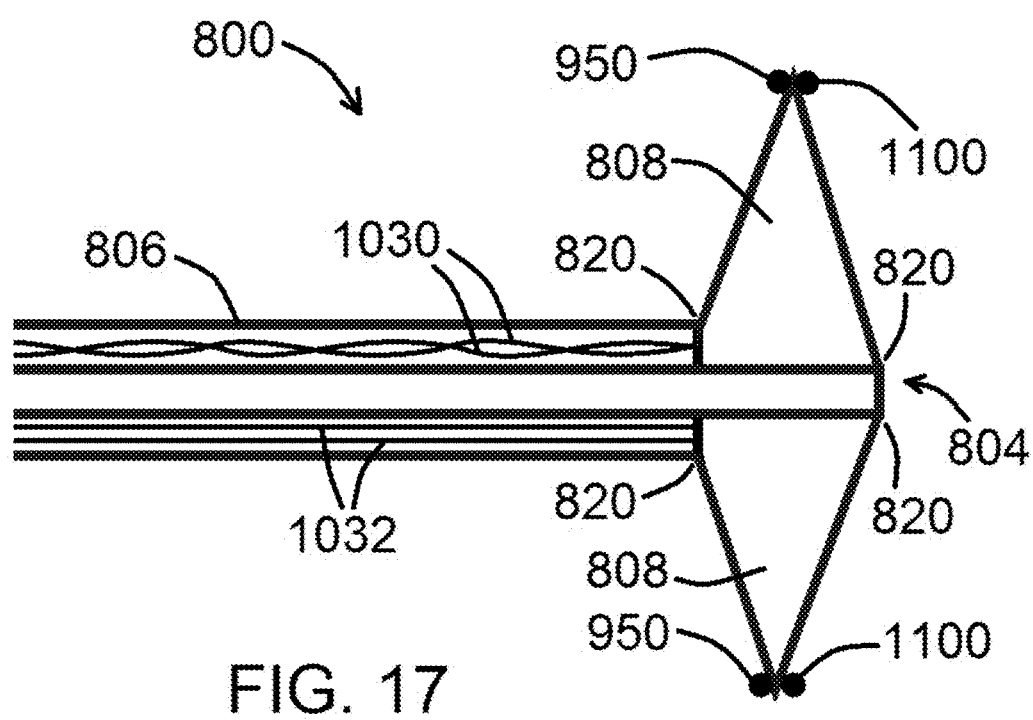

The amount of expansion may also be determined by electromagnetic field measurement systems, which are also currently employed for navigation in electrophysiology laboratories as well as orthopedic procedures. In such an embodiment, and as shown in the exemplary distal portion of a device 800 shown in FIG. 17, a small coil 1100 is placed at or near the tip of finger 808, the distal tip 804 of catheter body 806, and/or at hinge points 820. Each coil 1100 is connected to the measurement system (an exemplary data acquisition system 100 of the present disclosure) by a twisted pair of wires 1030 running to the proximal end 802 of the catheter body 806 and is configured to determine an expansion amount using electromagnetic field measurements by way of generating an electromagnetic field, as referenced below, detectable using one or more of the electrodes referenced herein. The amount of expansion may also be determined by piezoelectric sensors 950 (as referenced above, and positioned as described above) so that each crystal 950 is connected to the measurement system (data acquisition system 100) by a pair of wires 1032 running to the proximal end 802 of the catheter body 806. A short signal can be sent to a first crystal 950 to create an ultrasonic wave in the fluid surrounding the distal catheter assembly (device 800). A short time later, the ultrasonic wave reaches a second crystal 950, and reception of the wave causes a signal to be generated in the second crystal 950. The time between the signal being sent to the first crystal 950 and detected in the second crystal 950 is the transmission time of the ultrasonic wave. The transmission time depends on the speed of the ultrasonic wave in the fluid surrounding the catheter assembly (device 800) and the distance between the first and the second crystals 950. Size of a vessel lumen or an orifice may be gauged by positioning the distal end 804 of the catheter assembly (device 800) in the volume of interest, expanding the finger(s) 808 of device 800 and stopping the expansion when the finger(s) 808 reach the interior of the lumen or the annulus of the orifice. Determination that the finger(s) 808 have reached the aforementioned position may be inferred from mechanical resistance having been encountered when utilizing control wire 810 or inner shaft 900.

Figure 18:
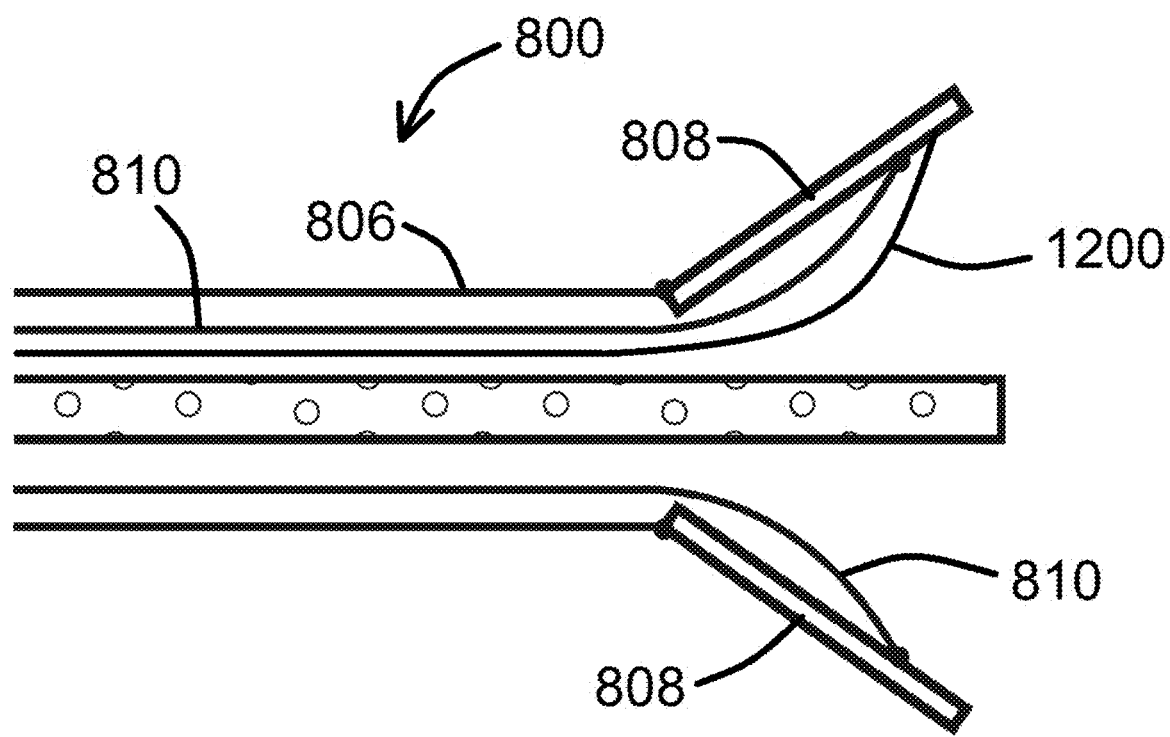

To quantify the mechanical resistance, a force measuring apparatus 1200, such as a spring scale or strain gauge, for example, is placed in series with the control wire 810 (as shown in FIG. 18) or inner shaft 900. The operator exerts tensile force upon the scale/strain gauge (apparatus 1200) to expand finger(s) 808 of device 800. Determination that the finger(s) 808 have reached the interior of the lumen or the annulus of an orifice may also be determined from impedance measured between single electrode 1000, 1002 placed at the tip of finger 808 and at the distal tip 804 of catheter body 806 or between single electrodes 1000, 1002 placed at one hinge point 820 and an electrode placed at another hinge point 820. Measured impedance between these pairs of electrodes 1000, 1002 reveals whether the electrodes 1000, 1002 are fully within a blood stream or have engaged tissue, as electrical impedance of tissue is higher than that of blood. Electrodes 1000, 1002 in a bloodstream present a lower impedance than electrodes 1000, 1002 touching tissue. When expanding finger(s) 808 of device 800, a rise in impedance between electrodes 1000, 1002 signals the electrodes 1000, 1002 have contacted tissue.

Determination that the finger(s) 808 have reached the interior of the lumen or the annulus of an orifice may also be determined from the electrogram measured between single electrodes 1000, 1002 placed at the tip of finger 808 and at the distal tip 804 of catheter body 806 or between single electrodes 1000, 1002 placed at first and second hinge points 820. If the volume of interest is within the heart, electrogram potentials will increase significantly when touching tissue as compared to when the electrodes 1000, 1002 are floating in the bloodstream.

Figure 19:
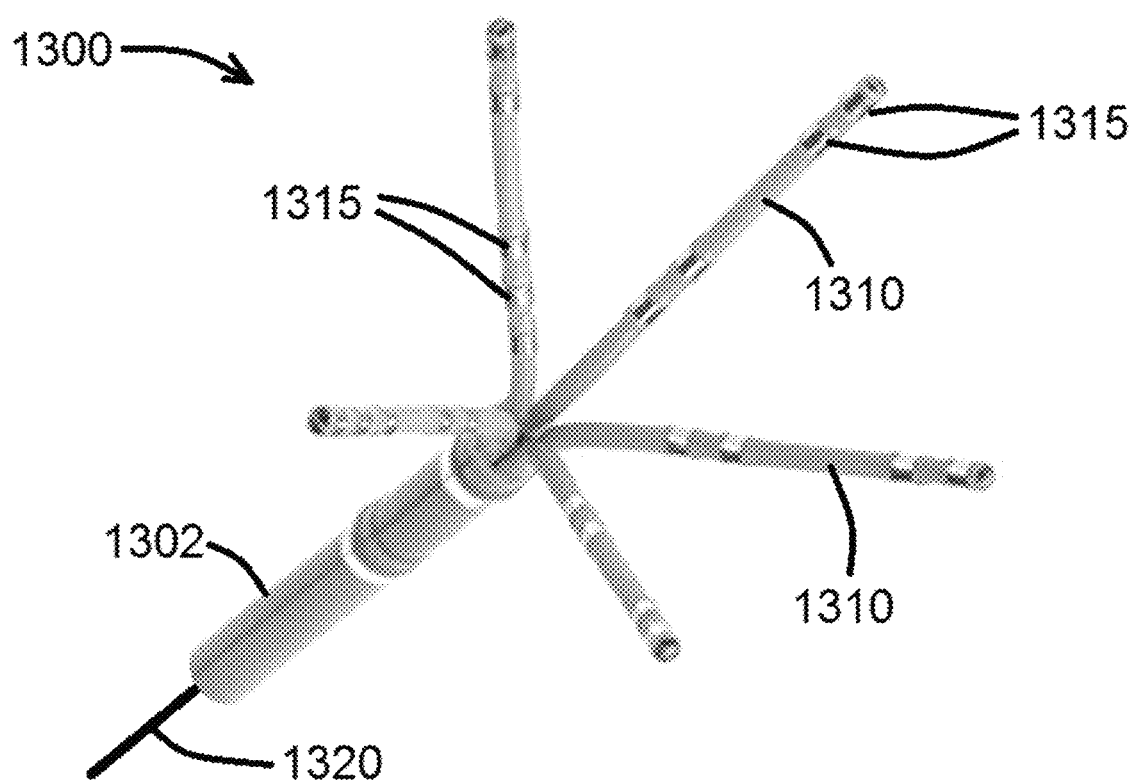
FIGS. 19, 20, and 21 show perspective views of at least part of sizing devices, according to exemplary embodiments of the present disclosure.

Additional devices for use with sizing luminal organs of the present disclosure are described as follows. Additional devices for use with sizing luminal organs of the present disclosure are described as follows. FIG. 19 shows an exemplary device 1300 of the present disclosure (which may have one or more components/features as other devices of the present disclosure, including, but not limited to, catheters 20, 21, 22, 39, wire 19, devices 500, 800, etc.), with said device comprising an elongated body 1302 and a plurality of linear extensions 1310 (also referred to herein as legs 1310). To measure a bore (luminal organ, bodily aperture, etc.), each linear extension 1310 may comprise one, two, or more electrodes 1315 ((which may be any number/type of electrodes referenced herein)). FIG. 19 shows an exemplary device 1300 having five linear extensions 1310, noting that less or more linear extensions 1310 may be used, with each linear extension 1310 having four or five electrodes therein, noting that more or fewer electrodes may be used.

In at least one embodiment, linear extensions 1310 are connected to a push/pull wire 1320 within catheter body 1302 of a device 1300. Device 1300 is configured for placement within a vessel 550 or other aperture/area within a body for sizing. Linear extensions 1310 are then extended and the position of the push/pull wire 1320 noted, such as the wire 1320 having indicia 814 thereon as shown in FIGS. 12A and 12C. Linear extensions 1310 may be calibrated before and/or after the sizing.

A manual control for the extension and/or retraction of linear extensions 1310 could be calibrated. Further, device 1300 could be constructed to be radiopaque and viewable on x-ray, fluoroscopy, CT, etc. Crystals (such as crystals 950 referenced herein) could be placed at or near the tips of each linear extension 1310, the crystals 950 connected to circuitry (such as wires 1010 and/or data acquisition system 100, as referenced herein, or other suitable circuitry) to emit ultrasonically for detection by a diagnostic ultrasound machine. A 3D ultrasound machine could locate signals from the tip of each linear extension 1310 while the tips of linear extensions 1310 are in the volume of interest. With known position of the tips, the lumen/annulus interior may be sized.

Three-dimensional electroanatomic mapping is widely used in the field of electrophysiology. Competing technologies used include impedance and electrically drive magnetic field detection. Orthogonal electric fields are created within the body for impedance-based systems. Electrodes are mapped within the body by measuring electrode voltage. Magnetic field systems create fields using coil radiators (coils 1100 of the present disclosure). Tiny coils placed on catheters are mapped within the body by measuring induced signals. Such mapping systems can be used to size areas within the body. A catheter with electrodes, i.e., pacing or diagnostic catheter, may be threaded into a volume of interest. With the use of steering mechanisms, the volume of interest may be explored. Recording the position within the body of the catheter, providing a summary of known positions reveals the extent of the explored volume and, thus, its size. Such exploration has been shown to be useful, for example, to map the annulus of the tricuspid valve.

Figure 20:
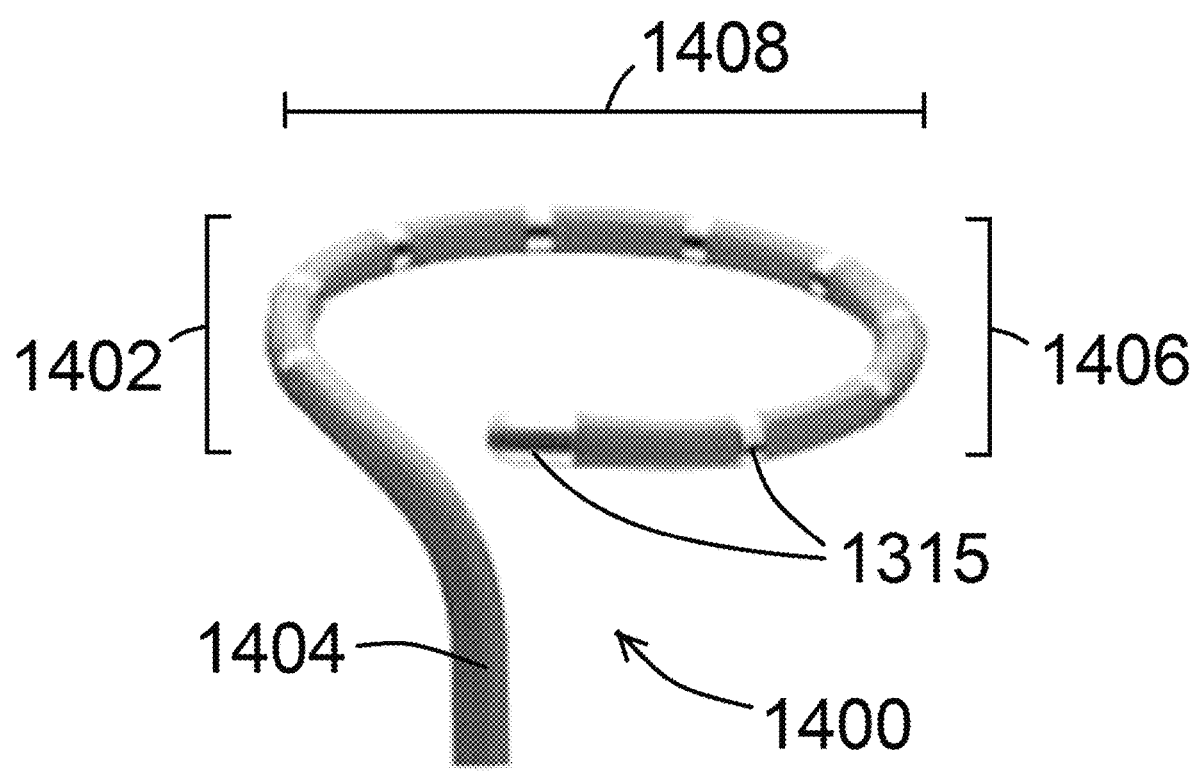

A type of catheter that may be especially useful in defining the annulus of a heart valve and potentially also used for ablation of the pulmonary veins in the treatment of atrial fibrillation is now referenced. As shown in FIG. 20, an exemplary device 1400 of the present disclosure is shown having a plurality of electrodes 1315 at a distal region 1402 of device 1400. Device 1400 comprises an elongated device body 1404 that, at distal region 1402, forms a circular configuration 1406 extending at least 180° around (shown as being more than 270° around and at or approaching 360° around in the figure).

Calibration is straightforward as inter-electrode spacing (the spacing between adjacent electrodes 1315) is defined at time of manufacture. Such devices 1400 (catheters or wires) can be steered and the loop diameter 1408 controlled during manipulation of the device 1400 within the body. To measure the annulus of a tricuspid valve, for example, the device 1400 could be advanced to the right ventricle. As the device 1400 is withdrawn across the tricuspid valve to the right atrium, the loop 1406 may distort as it passes the annulus. Recording positions of the electrodes 1315 as the device 1400 is manipulated in the vessel of interest provides the extent of the vessel and its size.

Figure 21:
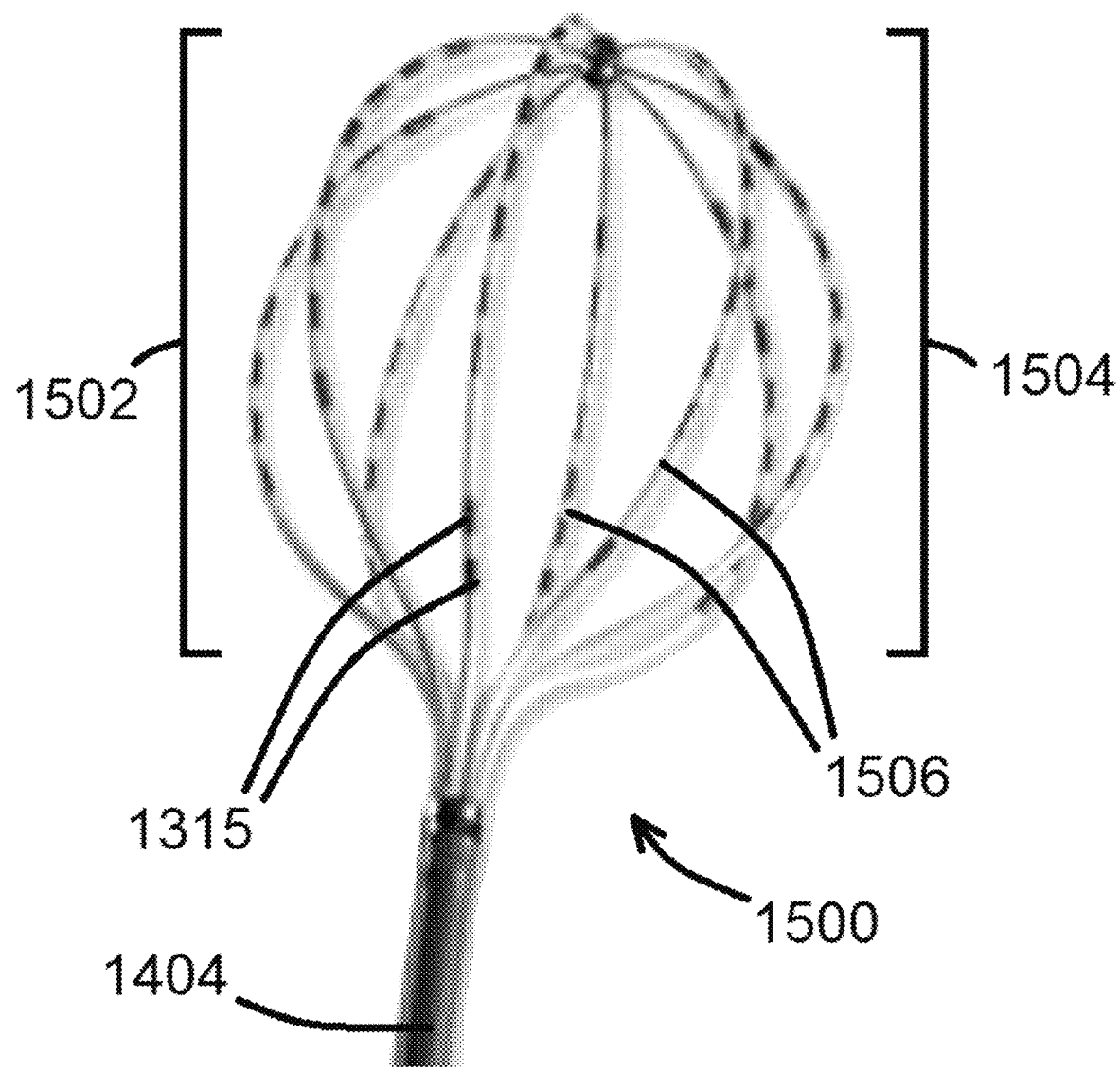

FIG. 21 shows an additional embodiment of an exemplary device of the present disclosure. As shown in FIG. 21, device 1500, also referred to herein as a basket device or a basket catheter, comprises an elongated device body 1404 that, at a distal region 1502, forms a bulbous configuration 1504 comprising a plurality of curved arms 1506. A plurality of electrodes 1315 may be present upon one or more curved arms 1506, similar to a plurality of electrodes 1315 present upon one or more linear extensions 1310 shown in FIG. 19. Such devices 1500 may be controlled remotely. This type of device 1500 may provide improved accuracy for example, in sizing a valve annulus or valve aperture, particularly if the annulus is not normal to the exploration/sizing device 1500. As in the embodiments referenced above, this type of device 1500 also lends itself to visualization with a 3D electroanatomic navigation system. For elements with position sensors for an electromagnetic field, such a field can be created as part of the overall navigation system. Also, and for elements with position sensors using electrodes, voltage gradients are created within the luminal organ, for example, as part of the navigation system.

Various device embodiments of the present disclosure can be used consistent with cardiac rhythm patterns. For example, current valvuloplasty methods rapidly pace the heart for a brief period of time (a few seconds, for example), so to eliminate ventricular contractions and avoid ejection against an inflated balloon. Methods of using various devices of the present disclosure to perform cardiac valve sizing can similarly rapidly pace the heart in connection therewith, for example, so to do away with the ventricular contraction just for a few moments to make accurate measurements using the device. In at least one embodiment of a method of obtaining a cardiac valve size, adenosine may be administered to the subject, so that ventricular contraction would be eliminated for a few seconds, for example, allowing for more precise measurements using the device. Regarding use of adenosine, for example, tricuspid and mitral annuli contract synchronously with ventricular contraction. A few seconds of ventricular asystole provide an opportunity to measure free of ventricular contraction and, therefore, measurement of diastolic annulus size. The administration of a pharmacologic agent such as adenosine would be via conventional techniques, i.e. vial, syringe, IV, etc.

Furthermore, and with respect to patients with low flow rates, accurate measurements of valve gradients are more difficult to obtain as compared to patients with normal flow. To address this concern, the present disclosure includes disclosure of techniques useful to create higher flow across a valve for the purpose of obtaining a gradient measurement so to calculate cross-sectional area (CSA) at that location. One technique includes a "push" (relatively rapid injection) of a fluid (such as saline) upstream of the valve, where measurements using the desired device can be made during the push. A second exemplary technique uses a series of two balloons. In the example of a tricuspid valve, a first balloon blocks outflow from the right atrium across the tricuspid valve, and a second balloon is in the superior vena cava (SVC). The first balloon is inflated and the right atrium is allowed to fill. After a brief period, such as two or three seconds for example, the first balloon is deflated and at the same time the second balloon is inflated. The second balloon is pushed down the SVC towards the right atrium. Thus, a pooling of blood occurs in the right atrium, during the two or three second filing period. The pool of blood is pushed across the tricuspid valve and pressure measurements are made during the push. Such a method allows for a more accurate assessment of CSA in patients with low cardiac output. Such a method can be performed using a separate balloon device in connection with an exemplary device of the present disclosure, for example. A third technique may use a single balloon, such as a long thin balloon placed in the SVC that when deflated would have negligible effect on flow. The balloon could be made with less compliance on a proximal section/more compliance on a distal portion, for example. Upon inflation, the balloon would first expand proximally and then extend distally. This peristaltic mechanism would push blood distally, towards the right atrium and across the tricuspid valve. A similar design could be utilized for other valves, for example.

Figure 22:
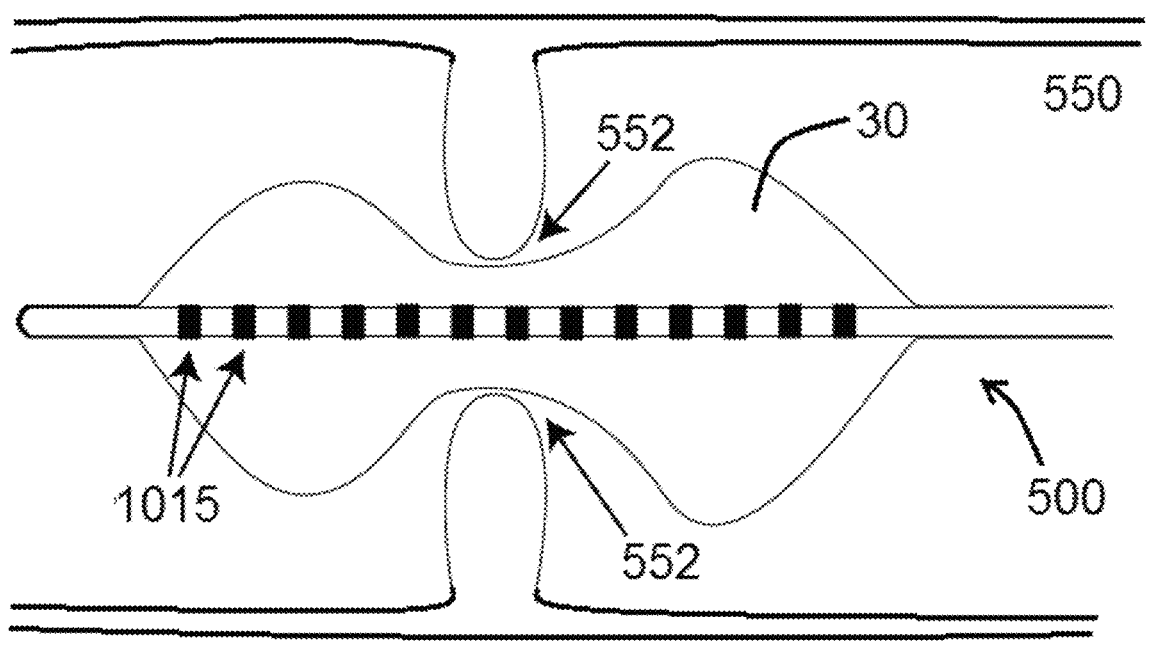
FIG. 22 shows a side view of at least part of a sizing device having a balloon positioned within a luminal organ at a valve annulus, according to an exemplary embodiment of the present disclosure.

As referenced herein, and in connection with valve annulus 552 measurements, device embodiments using a balloon 30 having electrodes therein can be filled with a fluid of known conductivity, and conductance measurements can be obtained between various electrodes within balloon 30, as shown in FIG. 9A and referenced herein. Said conductance measurements, as referenced herein, can provide information sufficient to determine valve annulus 552 CSA, corresponding to balloon CSA at the location(s) between various electrodes. As valve annuluses 552 can have various shapes, with most not being circular (having an irregular shape), various devices of the present disclosure are configured to obtain CSA measurements of non-circular valve apertures and luminal organs. Depending on the number of electrodes within the balloon 30, such as device 500 embodiments (or other device embodiments of the present disclosure) having more than four electrodes 1015 (as shown in FIG. 22), when balloon 30 is placed at a valve annulus 552, CSAs of balloon 30 can be obtained proximal to, at, and/or distal to the valve annulus 552 itself. For example, currently can be applied between various electrodes within balloon 30, and voltage can be measured across the same, so to obtain various CSAs in connection with, for example, various stages of balloon inflation. Depending on the location of valve annulus 552 along balloon 30, for example, valve annulus 552 may be at an electrode or between two electrodes, permitting movement of balloon 30 relative to valve annulus 552 so to obtain as precise of a measurement as desired. Adjusting balloon 30 position by an amount equal to one-half the inter-electrode spacing and repeating the circumferential measurement and comparing measurements provides an understanding of balloon/electrode position relative to the annulus 552. If, after adjustment, the measured diameter is larger, the balloon 30 position can be adjusted by an amount equal to the inter-electrode spacing, but in the opposite direction to the first position adjustment. Comparing serial measurements and finding the position at which the diameter is the smallest identifies the position at which the annulus measurement should be taken. Using multiple, close-spaced electrodes may obviate the need for multiple position measurements. Measuring between closely spaced pairs of electrodes reveals a balloon 30 diameter/circumference profile along the balloon 30.

Furthermore, and with respect to pressures, various pressures can be measured, including measuring pressure with a lumen in the catheter to the balloon, a lumen in the catheter to a distal port on the catheter and outside of the balloon, or a pressure transducer within the balloon, and detecting passage of the catheter from one chamber to another by a change in pressure (pulse pressure, mean pressure or other). With a balloon 30 capable of extending to both sides of an annulus 552 (as shown in FIGS. 9A and 22), this allows positioning a balloon 30 rapidly so the central and least restrained portion of the balloon 30 is free to expand to the interior dimensions of an annulus 552. Rapid positioning and measurement may be important as a balloon method of sizing obstructs blood flow.

Again, it is noted that the various devices, systems, and methods described herein can be applied to any body lumen or treatment site. For example, the devices, systems, and methods described herein can be applied to any one of the following exemplary bodily hollow organs: the cardiovascular system including the heart, the digestive system, the respiratory system, the reproductive system, and the urogenital tract.

While various embodiments of devices, systems, and methods for measuring a percutaneous valve and/or valve annulus using a balloon sizing device have been described in considerable detail herein, the embodiments are merely offered by way of non-limiting examples of the disclosure described herein. It will therefore be understood that various changes and modifications may be made, and equivalents may be substituted for elements thereof, without departing from the scope of the disclosure. Indeed, this disclosure is not intended to be exhaustive or to limit the scope of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A device for obtaining measurements within a luminal organ, comprising:
an elongated body;
a first sizing finger and a second sizing finger, each comprising a proximal end and an unattached distal tip, the proximal end positioned at a distal end of the elongated body and the first sizing finger and the second sizing finger each configured to move from a first position to a second position by way of adjustment of at least one movable device coupled thereto, wherein the at least one movable device comprises a first control wire coupled to the first sizing finger and a second control wire coupled to the second sizing finger, wherein the first control wire is configured to move the first sizing finger independently from the second sizing finger controlled by the second control wire, and wherein the proximal end of each of the first sizing finger and the second sizing finger is hingedly coupled to the elongated body;
a first electrode positioned upon the first sizing finger;
a second electrode positioned upon the second sizing finger; and
a third electrode and a fourth electrode positioned along the elongated body proximal to the first and second sizing fingers and separated a known distance from one another;
wherein a first dimensional measurement within the luminal organ can be determined based upon the first position and the second position of each of the first sizing finger and the second sizing finger, the first dimensional measurement indicative of a measurement along a first axis; and wherein an additional dimensional measurement within the luminal organ can be obtained using the third electrode and the fourth electrode, based in part upon the known distance between the third electrode and the fourth electrode and a voltage difference between the third electrode and the fourth electrode, the additional dimensional measurement indicative of a measurement along a second axis orthogonal to the first axis.

2. The device of claim 1, further comprising at least one force measuring apparatus coupled to each of the first sizing finger and the second sizing finger, the at least one force measuring apparatus configured to quantify mechanical resistance of each of the first sizing finger and the second sizing finger relative to a wall of the luminal organ.

3. The device of claim 1, whereby a first difference in voltage obtained using the first electrode and the second electrode can be obtained using the device, whereby a second difference in voltage obtained using the third electrode and the fourth electrode can be obtained using the device, the first voltage difference and the second voltage difference being a function of at least one distance between two or more of the first electrode, the second electrode, the third electrode, and/or the fourth electrode.

4. The device of claim 1, further comprising a first coil positioned upon one of the first sizing finger or the second sizing finger, the first coil configured to generate a magnetic field detectable using at least one of the first electrode, the second electrode, or an additional electrode positioned upon a portion of the device.

5. The device of claim 1, further comprising a first piezoelectric sensor positioned upon the first sizing finger and a second piezoelectric sensor positioned upon the second sizing finger, the first piezoelectric sensor configured to generate an ultrasonic wave detectable by the second piezoelectric sensor, whereby a transmission time of the ultrasonic wave is indicative of a distance between the first piezoelectric sensor and the second piezoelectric sensor, which is indicative of the dimensional measurement.

6. The device of claim 1, wherein the third electrode and the fourth electrode are configured to detect an electric field within the luminal organ to generate impedance data, wherein the impedance data and a known distance between the third electrode and the fourth electrode are used to determine the dimensional measurement.

7. A device for obtaining measurements within a luminal organ, comprising:
an elongated body;
a first sizing finger and a second sizing finger, each comprising a proximal end and an unattached distal tip, the proximal end positioned at a distal end of the elongated body and the first sizing finger and the second sizing finger each configured to move from a first position to a second position by way of adjustment of at least one movable device coupled thereto, wherein the at least one movable device comprises a first control wire coupled to the first sizing finger and a second control wire coupled to the second sizing finger, wherein the first control wire is configured to move the first sizing finger independently from the second sizing finger controlled by the second control wire, and wherein the proximal end of each of the first sizing finger and the second sizing finger is hingedly coupled to the elongated body;
a first electrode positioned upon the first sizing finger;
a second electrode positioned upon the second sizing finger; and
a third electrode and a fourth electrode positioned along the elongated body proximal to the first and second sizing fingers and separated a known distance from one another;
wherein a first dimensional measurement within the luminal organ can be determined based upon the first position and the second position of each of the first sizing finger and the second sizing finger, the dimensional measurement selected from the group consisting of a cross-sectional area of the luminal organ, a valve aperture dimensional measurement, and a valve annulus dimensional measurement; and
wherein an additional dimensional measurement within the luminal organ can be obtained using the third electrode and the fourth electrode, based in part upon the known distance between the third electrode and the fourth electrode and a voltage difference between the third electrode and the fourth electrode, the additional dimensional measurement indicative of a measurement along a second axis orthogonal to a first axis.

8. The device of claim 7, whereby a first difference in voltage obtained using the first electrode and the second electrode can be obtained using the device.

9. A method for obtaining measurements within a luminal organ, comprising the steps of:
positioning at least part of a device within a luminal organ, the device comprising:
an elongated body,
a first sizing finger and a second sizing finger, each comprising a proximal end and an unattached distal tip, the proximal end positioned at a distal end of the elongated body and the first sizing finger and the second sizing finger each configured to move from a first position to a second position by way of adjustment of at least one movable device coupled thereto, wherein the at least one movable device comprises a first control wire coupled to the first sizing finger and a second control wire coupled to the second sizing finger, wherein the first control wire is configured to move the first sizing finger independently from the second sizing finger controlled by the second control wire, and wherein the proximal end of each of the first sizing finger and the second sizing finger is hingedly coupled to the elongated body;
a first electrode positioned upon the first sizing finger,
a second electrode positioned upon the second sizing finger, and
a third electrode and a fourth electrode positioned along the elongated body proximal to the first and second sizing fingers and separated a known distance from one another,
wherein a first dimensional measurement within the luminal organ can be determined based upon the first position and the second position of each of the first sizing finger and the second sizing finger, the first dimensional measurement indicative of a measurement along a first axis, and
wherein an additional dimensional measurement within the luminal organ can be obtained using the third electrode and the fourth electrode, based in part upon the known distance between the third electrode and the fourth electrode and a voltage difference between the third electrode and the fourth electrode, the additional dimensional measurement indicative of a measurement along a second axis orthogonal to the first axis;

moving the at least one movable device in a first direction to cause each of the first sizing finger and the second sizing finger to move from the first position to the second position; and determining the first dimensional measurement within the luminal organ based upon the first position and the second position of each of the first sizing finger and the second sizing finger; and obtaining the additional dimensional measurement within the luminal organ using the third electrode and the fourth electrode.

10. The method of claim 9, wherein the determining step includes the step of identifying a distance of movement of the at least one movable device based upon indicia of the at least one movable device.

11. The method of claim 9, wherein the determining step includes the step of obtaining a first voltage measurement between the first electrode and the second electrode.

12. The method of claim 9, wherein the moving step is performed to cause each of the first sizing finger and the second sizing finger to move from the first position of being relatively aligned with the elongated body to the second position of extending from the elongated body so that at least part of each of the first sizing finger and the second sizing finger contacts a wall of the luminal organ.

13. The method of claim 9, wherein the moving step is performed to cause the first sizing finger and the second sizing finger to move from the first position of being within the elongated body to the second position of extending from the elongated body so that at least part of each of the first sizing finger and the second sizing finger contact a wall of the luminal organ.

* * * * *